United States Patent
Yang et al.

(10) Patent No.: US 9,572,663 B2
(45) Date of Patent: Feb. 21, 2017

(54) METHODS AND APPARATUSES FOR DEPLOYING MINIMALLY-INVASIVE HEART VALVES

(71) Applicant: Edwards Lifesciences Corporation, Irvine, CA (US)

(72) Inventors: Jibin Yang, Aliso Viejo, CA (US); Scott H. Heneveld, Sr., Redding, CA (US); Matthew L. Pease, Mountain View, CA (US); Brandon G. Walsh, Livermore, CA (US)

(73) Assignee: Edwards Lifesciences Corporation, Irvine, CA (US)

( * ) Notice: Subject to any disclaimer, the term of this patent is extended or adjusted under 35 U.S.C. 154(b) by 225 days.

(21) Appl. No.: 14/203,258

(22) Filed: Mar. 10, 2014

(65) Prior Publication Data
US 2014/0194977 A1      Jul. 10, 2014

Related U.S. Application Data

(63) Continuation of application No. 13/350,730, filed on Jan. 13, 2012, now Pat. No. 9,452,046, which is a
(Continued)

(51) Int. Cl.
*A61F 2/95*         (2013.01)
*A61F 2/24*         (2006.01)

(52) U.S. Cl.
CPC ............ *A61F 2/243* (2013.01); *A61F 2/2409* (2013.01); *A61F 2/2412* (2013.01); *A61F 2/2427* (2013.01)

(58) Field of Classification Search
CPC ............ A61F 2002/30293; A61F 2002/5067; A61F 2/92; A61F 2/93; A61F 2/95; A61F 2002/9522; A61F 2/2427; A61F 2/243; A61F 2/2439
See application file for complete search history.

(56) References Cited

U.S. PATENT DOCUMENTS 3,409,013 A    11/1968   Berry
3,472,230 A    10/1969   Fogarty et al.
(Continued)

FOREIGN PATENT DOCUMENTS

DE        2246526       3/1973
DE       19532846      3/1997
(Continued)

OTHER PUBLICATIONS

Andersen, et al., "Transluminal implantation of artificial heart valves. Description of a new expandable aortic valve and initial results with implantation by catheter technique in closed chest pigs." European Heart Journal (1992), 13, 704-708.
(Continued)

*Primary Examiner* — Christopher D Prone
(74) *Attorney, Agent, or Firm* — David L. Hauser

(57) ABSTRACT

Methods and systems for delivering and deploying a prosthetic heart valve include a deployment mechanism coupled to the prosthetic heart valve, the deployment mechanism having a longitudinal shaft that when rotated in a first direction, expands the prosthetic heart valve from a contracted state to an expanded state, and optionally, when rotated in a second direction opposite the first direction, re-contracts the prosthetic valve from the expanded state. Embodiments of the deployment mechanism include a pinion gear that engages a gear track on the prosthetic heart valve.

16 Claims, 22 Drawing Sheets

Related U.S. Application Data continuation of application No. 12/488,480, filed on Jun. 19, 2009, now Pat. No. 8,740,975, which is a continuation of application No. 09/951,701, filed on Sep. 13, 2001, now Pat. No. 7,556,646.

(56) References Cited

U.S. PATENT DOCUMENTS

| | | |
|---|---|---|
| 3,548,417 A | 12/1970 | Kisher |
| 3,587,115 A | 6/1971 | Shiley |
| 3,657,744 A | 4/1972 | Ersek |
| 3,671,979 A | 6/1972 | Moulopoulos |
| 3,714,671 A | 2/1973 | Edwards et al. |
| 3,739,402 A | 6/1973 | Cooley et al. |
| 3,755,823 A | 9/1973 | Hancock |
| 4,035,849 A | 7/1977 | Angell et al. |
| 4,056,854 A | 11/1977 | Boretos et al. |
| 4,106,129 A | 8/1978 | Carpentier et al. |
| 4,204,283 A | 5/1980 | Bellhouse et al. |
| 4,222,126 A | 9/1980 | Boretos et al. |
| 4,265,694 A | 5/1981 | Boretos et al. |
| 4,297,749 A | 11/1981 | Davis et al. |
| 4,339,831 A | 7/1982 | Johnson |
| 4,340,977 A | 7/1982 | Brownlee et al. |
| 4,343,048 A | 8/1982 | Ross et al. |
| 4,345,340 A | 8/1982 | Rosen |
| 4,373,216 A | 2/1983 | Klawitter |
| 4,406,022 A | 9/1983 | Roy |
| 4,470,157 A | 9/1984 | Love |
| 4,490,859 A | 1/1985 | Black et al. |
| 4,535,483 A | 8/1985 | Klawitter et al. |
| 4,574,803 A | 3/1986 | Storz |
| 4,592,340 A | 6/1986 | Boyles |
| 4,605,407 A | 8/1986 | Black et al. |
| 4,612,011 A | 9/1986 | Kautzky |
| 4,643,732 A | 2/1987 | Pietsch et al. |
| 4,655,771 A | 4/1987 | Wallsten |
| 4,692,164 A | 9/1987 | Dzemeshkevich et al. |
| 4,733,665 A | 3/1988 | Palmaz |
| 4,759,758 A | 7/1988 | Gabbay |
| 4,762,128 A | 8/1988 | Rosenbluth |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,829,990 A | 5/1989 | Thuroff et al. |
| 4,851,001 A | 7/1989 | Taheri |
| 4,856,516 A | 8/1989 | Hillstead |
| 4,878,495 A | 11/1989 | Grayzel |
| 4,878,906 A | 11/1989 | Lindemann et al. |
| 4,883,458 A | 11/1989 | Shiber |
| 4,922,905 A | 5/1990 | Strecker |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Sammuels |
| 5,059,177 A | 10/1991 | Towne et al. |
| 5,080,668 A | 1/1992 | Bolz et al. |
| 5,085,635 A | 2/1992 | Cragg |
| 5,089,015 A | 2/1992 | Ross |
| 5,147,370 A * | 9/1992 | McNamara ............... A61F 2/88 606/108 |
| 5,152,771 A | 10/1992 | Sabbaghian et al. |
| 5,163,953 A | 11/1992 | Vince |
| 5,167,628 A | 12/1992 | Boyles |
| 5,192,297 A | 3/1993 | Hull |
| 5,266,073 A | 11/1993 | Wall |
| 5,282,847 A | 2/1994 | Trescony et al. |
| 5,295,958 A | 3/1994 | Shturman |
| 5,332,402 A | 7/1994 | Teitelbaum |
| 5,344,425 A | 9/1994 | Sawyer |
| 5,360,444 A | 11/1994 | Kusuhara |
| 5,370,685 A | 12/1994 | Stevens |
| 5,397,351 A | 3/1995 | Pavcnik et al. |
| 5,411,055 A | 5/1995 | Kane et al. |
| 5,411,552 A | 5/1995 | Andersen et al. |
| 5,443,446 A | 8/1995 | Shturman |
| 5,480,424 A | 1/1996 | Cox |
| 5,500,014 A | 3/1996 | Quijano et al. |
| 5,545,209 A | 8/1996 | Roberts et al. |
| 5,545,214 A | 8/1996 | Stevens |
| 5,549,665 A | 8/1996 | Vesely |
| 5,554,185 A | 9/1996 | Block et al. |
| 5,556,413 A | 9/1996 | Lam |
| 5,571,175 A | 11/1996 | Vanney et al. |
| 5,591,185 A | 1/1997 | Kilmer et al. |
| 5,607,464 A | 3/1997 | Trescony et al. |
| 5,609,626 A | 3/1997 | Quijano et al. |
| 5,618,299 A | 4/1997 | Khosravi et al. |
| 5,639,274 A | 6/1997 | Fischell et al. |
| 5,665,115 A | 9/1997 | Cragg |
| 5,716,417 A | 2/1998 | Girard et al. |
| 5,728,068 A | 3/1998 | Leone et al. |
| 5,749,890 A | 5/1998 | Shaknovich |
| 5,756,476 A | 5/1998 | Epstein |
| 5,769,812 A | 6/1998 | Stevens et al. |
| 5,800,508 A | 9/1998 | Goicoechea et al. |
| 5,840,081 A | 11/1998 | Andersen et al. |
| 5,855,597 A | 1/1999 | Jayaraman |
| 5,855,601 A | 1/1999 | Bessler |
| 5,855,602 A | 1/1999 | Angell |
| 5,925,063 A * | 7/1999 | Khosravi ......... A61B 17/12022 606/157 |
| 5,957,929 A * | 9/1999 | Brenneman ............... A61F 2/92 606/1 |
| 5,957,949 A | 9/1999 | Leonhardt et al. |
| 5,968,068 A | 10/1999 | Dehdashtian |
| 5,980,570 A | 11/1999 | Simpson |
| 5,984,959 A | 11/1999 | Robertson et al. |
| 6,027,525 A | 2/2000 | Suh et al. |
| 6,042,607 A | 3/2000 | Williamson, IV et al. |
| 6,132,473 A | 10/2000 | Williams et al. |
| 6,168,614 B1 | 1/2001 | Andersen et al. |
| 6,168,616 B1 | 1/2001 | Brown, III |
| 6,171,335 B1 | 1/2001 | Wheatley et al. |
| 6,174,327 B1 | 1/2001 | Mertens et al. |
| 6,210,408 B1 | 4/2001 | Chandrasakaran et al. |
| 6,217,585 B1 | 4/2001 | Houser et al. |
| 6,221,091 B1 | 4/2001 | Khosravi |
| 6,231,602 B1 | 5/2001 | Carpentier et al. |
| 6,245,102 B1 | 6/2001 | Jayaraman |
| 6,299,637 B1 | 10/2001 | Shaolian |
| 6,302,906 B1 | 10/2001 | Goecoechea et al. |
| 6,312,465 B1 | 11/2001 | Griffin et al. |
| 6,350,277 B1 | 2/2002 | Kocur |
| 6,358,277 B1 | 3/2002 | Duran |
| 6,379,372 B1 | 4/2002 | Dehdashtian et al. |
| 6,425,916 B1 | 7/2002 | Garrison et al. |
| 6,440,164 B1 | 8/2002 | Di Matteo et al. |
| 6,454,799 B1 | 9/2002 | Schreck |
| 6,458,153 B1 | 10/2002 | Bailey et al. |
| 6,461,382 B1 | 10/2002 | Cao |
| 6,468,660 B2 | 10/2002 | Ogle |
| 6,482,228 B1 | 11/2002 | Norred |
| 6,488,704 B1 | 12/2002 | Connelly et al. |
| 6,569,196 B1 | 5/2003 | Vesely et al. |
| 6,582,462 B1 | 6/2003 | Andersen et al. |
| 6,605,112 B1 | 8/2003 | Moll |
| 6,629,534 B1 | 10/2003 | St. Goar et al. |
| 6,723,122 B2 | 4/2004 | Yang |
| 6,730,118 B2 | 5/2004 | Spenser et al. |
| 6,733,525 B2 | 5/2004 | Yang et al. |
| 6,790,229 B1 | 9/2004 | Berreklouw |
| 6,830,584 B1 | 12/2004 | Seguin |
| 6,893,460 B2 | 5/2005 | Spenser et al. |
| 6,908,481 B2 | 6/2005 | Cribier |
| 7,018,406 B2 | 3/2006 | Seguin et al. |
| 7,276,078 B2 | 10/2007 | Spenser et al. |
| 7,276,084 B2 | 10/2007 | Yang et al. |

(56) References Cited

U.S. PATENT DOCUMENTS

| | | | |
|---|---|---|---|
| 7,318,278 | B2 | 1/2008 | Zhang et al. |
| 7,374,571 | B2 | 5/2008 | Pease et al. |
| 7,381,210 | B2 | 6/2008 | Zarbatany et al. |
| 7,393,360 | B2 | 7/2008 | Spenser et al. |
| 7,462,191 | B2 | 12/2008 | Spenser et al. |
| 7,510,575 | B2 | 3/2009 | Spenser et al. |
| 7,579,381 | B2 | 8/2009 | Dove |
| 7,585,321 | B2 | 9/2009 | Cribier |
| 7,618,446 | B2 | 11/2009 | Andersen et al. |
| 7,621,948 | B2 | 11/2009 | Herrmann |
| 7,993,394 | B2 | 8/2011 | Hariton et al. |
| 8,007,992 | B2 | 8/2011 | Tian et al. |
| 8,029,556 | B2 | 10/2011 | Rowe |
| 8,167,932 | B2 | 5/2012 | Bourang |
| 2001/0021872 | A1 | 9/2001 | Bailey et al. |
| 2002/0032481 | A1 | 3/2002 | Gabbay |
| 2002/0049370 | A1 | 4/2002 | Laufer et al. |
| 2002/0173842 | A1 | 11/2002 | Buchanan |
| 2003/0050694 | A1 | 3/2003 | Yang et al. |
| 2003/0100939 | A1 | 5/2003 | Yodfat et al. |
| 2003/0120333 | A1 | 6/2003 | Ouriel et al. |
| 2003/0212454 | A1 | 11/2003 | Scott et al. |
| 2004/0039436 | A1 | 2/2004 | Spenser et al. |
| 2004/0133263 | A1 | 7/2004 | Dusbabek et al. |
| 2004/0186565 | A1 | 9/2004 | Schreck |
| 2004/0260389 | A1 | 12/2004 | Case et al. |
| 2005/0033398 | A1 | 2/2005 | Seguin |
| 2005/0203614 | A1 | 9/2005 | Forster et al. |
| 2005/0203617 | A1 | 9/2005 | Forster et al. |
| 2005/0234546 | A1 | 10/2005 | Nugent et al. |
| 2005/0288766 | A1 | 12/2005 | Plain et al. |
| 2006/0025857 | A1 | 2/2006 | Bergheim et al. |
| 2006/0149350 | A1 | 7/2006 | Patel et al. |
| 2006/0229719 | A1 | 10/2006 | Marquez et al. |
| 2006/0259137 | A1 | 11/2006 | Artof et al. |
| 2007/0005131 | A1 | 1/2007 | Taylor |
| 2007/0005231 | A1 | 1/2007 | Seguchi |
| 2007/0010877 | A1 | 1/2007 | Salahieh et al. |
| 2007/0112422 | A1 | 5/2007 | Dehdashtian |
| 2007/0203575 | A1 | 8/2007 | Forster et al. |
| 2007/0270943 | A1 | 11/2007 | Solem |
| 2008/0065011 | A1 | 3/2008 | Marchand et al. |
| 2008/0114442 | A1 | 5/2008 | Mitchell et al. |
| 2008/0154355 | A1 | 6/2008 | Benichou et al. |
| 2008/1061911 | | 7/2008 | Revuelta et al. |
| 2009/0157175 | A1 | 6/2009 | Benichou |
| 2009/0164005 | A1 | 6/2009 | Dove et al. |
| 2009/0171456 | A1 | 7/2009 | Kveen et al. |
| 2009/0281619 | A1 | 11/2009 | Le et al. |
| 2009/0319037 | A1 | 12/2009 | Rowe et al. |
| 2010/0049313 | A1 | 2/2010 | Alon et al. |
| 2010/0204781 | A1 | 8/2010 | Alkhatib |
| 2011/0015729 | A1 | 1/2011 | Jimenez et al. |
| 2012/0123529 | A1 | 5/2012 | Levi et al. |

FOREIGN PATENT DOCUMENTS

| | | |
|---|---|---|
| DE | 19546692 | 6/1997 |
| DE | 19857887 | 7/2000 |
| DE | 19907646 | 8/2000 |
| DE | 10049812 | 4/2002 |
| DE | 10049813 | 4/2002 |
| DE | 10049814 | 4/2002 |
| DE | 10049815 | 4/2002 |
| EP | 0103546 | 3/1984 |
| EP | 0144167 | 6/1985 |
| EP | 0597967 | 12/1994 |
| EP | 0592410 | 10/1995 |
| EP | 0850607 | 7/1998 |
| EP | 1057460 | 12/2000 |
| EP | 1088529 | 4/2001 |
| EP | 1570809 | 9/2005 |
| FR | 2788217 | 7/2000 |
| GB | 2056023 | 3/1981 |
| SU | 1271508 | 11/1986 |
| WO | WO 91/17720 | 11/1991 |
| WO | WO 92/17118 | 10/1992 |
| WO | WO 93/01768 | 2/1993 |
| WO | WO 97/24080 | 7/1997 |
| WO | WO 98/29057 | 7/1998 |
| WO | WO 99/33414 | 7/1999 |
| WO | WO 99/40964 | 8/1999 |
| WO | WO 99/47075 | 9/1999 |
| WO | WO 00/18333 | 4/2000 |
| WO | WO 00/41652 | 7/2000 |
| WO | WO 00/47139 | 8/2000 |
| WO | WO 01/35878 | 5/2001 |
| WO | WO 01/49213 | 7/2001 |
| WO | WO 01/54624 | 8/2001 |
| WO | WO 01/54625 | 8/2001 |
| WO | WO 01/62189 | 8/2001 |
| WO | WO 01/64137 | 9/2001 |
| WO | WO 01/76510 | 10/2001 |
| WO | WO 02/22054 | 3/2002 |
| WO | WO 02/36048 | 5/2002 |
| WO | WO 02/41789 | 5/2002 |
| WO | WO 02/43620 | 6/2002 |
| WO | WO 02/47575 | 6/2002 |
| WO | WO 02/49540 | 6/2002 |
| WO | WO 03/047468 | 6/2003 |
| WO | WO 2005/087140 | 9/2005 |
| WO | WO 2006/014233 | 2/2006 |
| WO | WO 2006/034008 | 3/2006 |
| WO | WO 2008/005405 | 1/2008 |
| WO | WO 2008/035337 | 3/2008 |
| WO | WO 2008/147964 | 12/2008 |
| WO | WO 2008/150529 | 12/2008 |

OTHER PUBLICATIONS

Andersen, Henning Rud, "History of Percutaneous Aortic Valve Prosthesis," Herz 34 2009 Nr. 5, Urban & Vogel, pp. 343-346, Skejby University Hospital Department of Cardiology, Aarhus, Denmark.

Almagor, M.D., Yaron, et al., "Balloon Expandable Stent Implantation in Stenotic Right Heart Valved Conduits," Journal of the American College of Cardiology, vol. 16, No. 6, pp. 1310-1314, Nov. 1, 1990; ISSN 0735-1097.

Sabbah, Ph.D., Hani N., et al., "Mechanical Factors in the Degeneration of Porcine Bioprosthetic Valves: An Overview," Journal of Cardiac Surgery, vol. 4, No. 4, pp. 302-309, Dec. 1989; ISSN 0886-0440.

Serruys, P.W., et al., "Stenting of Coronary Arteries. Are we the Sorcerer's Apprentice?," European Heart Journal (1989) 10, 774-782, pp. 37-45, Jun. 13, 1989.

Kolata, Gina, "Device That Opens Clogged Arteries Gets a Failing Grade in a New Study," nytimes.com, http://www.nytimes.com/1991/01/03/health/device-that-opens-clogged-arteries-gets-a-faili . . . , Jul. 29, 2009, 2 pages.

Urban, M.D., Philip, "Coronary Artery Stenting," Editions Médecine et Hygiène, Genève, 1991, pp. 5-47.

Al-Khaja, N., et al., "Eleven Years' Experience with Carpentier-Edwards Biological Valves in Relation to Survival and Complications," European Journal of Cardiothoracic Surgery 3:305-311, Jun. 30, 2009.

Wheatley, M.D., David J., "Valve Prostheses," Rob & Smith's Operative Surgery, Fourth Edition, pp. 415-424, Butterworths 1986.

Benchimol, Alberto, et al., "Simultaneous Left Ventricular Echocardiography and Aortic Blood Velocity During Rapid Right Ventricular Pacing in Man," The American Journal of the Medical Sciences, Jan.-Feb. 1977 vol. 273, No. 1, pp. 55-62.

Watt, A.H., et al. "Intravenous Adenosine in the Treatment of Supraventricular Tachycardia; a Dose-Ranging Study and Interaction with Dipyridamole," British Journal of Clinical Pharmacology (1986), 21, 227-230.

Uchida, Barry T., et al., "Modifications of Gianturco Expandable Wire Stents," AJR:150, May 1988, Dec. 3, 1987, pp. 1185-1187.

Selby, M.D., J. Bayne, "Experience with New Retrieval Forceps for Foreign Body Removal in the Vascular, Urinary, and Biliary Systems," Radiology 1990; 176:535-538.

(56) References Cited

OTHER PUBLICATIONS

Inoune, M.D., Kanji, et al., "Clinical Application of Transvenous Mitral Commissurotomy by a New Balloon Catheter," The Journal of Thoracic and Cardiovascular Surgery 87:394-402, 1984.
Al Zaibag, Muayed, et al., "Percutaneous Balloon Valvotomy in Tricuspid Stenosis," British Heart Journal, Jan. 1987, vol. 57, No. 1, pp. 51-53.
Dotter, M.D., Charles T., "Transluminal Treatment of Arteriosclerotic Obstruction," University of Oregon's Minthorn Memorial Laboratory for Cardiovascular Research through Radiology, Circulation, vol. XXX, Nov. 1964, pp. 654-670.
Sigwart, Ulrich, "An Overview of Intravascular Stents: Old and New," Chapter 48, Textbook of Interventional Cardiology, $2^{nd}$ Edition, W.B. Saunders Company, Philadelphia, PA, © 1994, 1990, pp. 803-815.
Rösch, M.D., Josef, "The Birth, Early Years and Future of Interventional Radiology," J Vasc Interv Radiol 2003; 14:841-853.
Pavcnik, M.D., Ph.D., Dusan, et al. "Development and Initial Experimental Evaluation of a Prosthetic Aortic Valve for Transcatheter Placement," Cardiovascular Radiology 1992; 183:151-154.
Ross, F.R.C.S., D.N., "Aortic Valve Surgery," Guy's Hospital, London, pp. 192-197, approximately 1968.
Rashkind, M.D., William J., "Creationof an Atrial Septal Defect Withoput Thoracotomy," the Journal of the American Medical Association, vol. 196, No. 11, Jun. 13, 1966, pp. 173-174.
Porstmann, W., et al., "Der Verschluβ des Ductus Arteriosus Persistens ohne Thorakotomie," Thoraxchirurgie Vaskuläre Chirurgie, Band 15, Heft 2, Stuttgart, im Apr. 1967, pp. 199-203.

\* cited by examiner

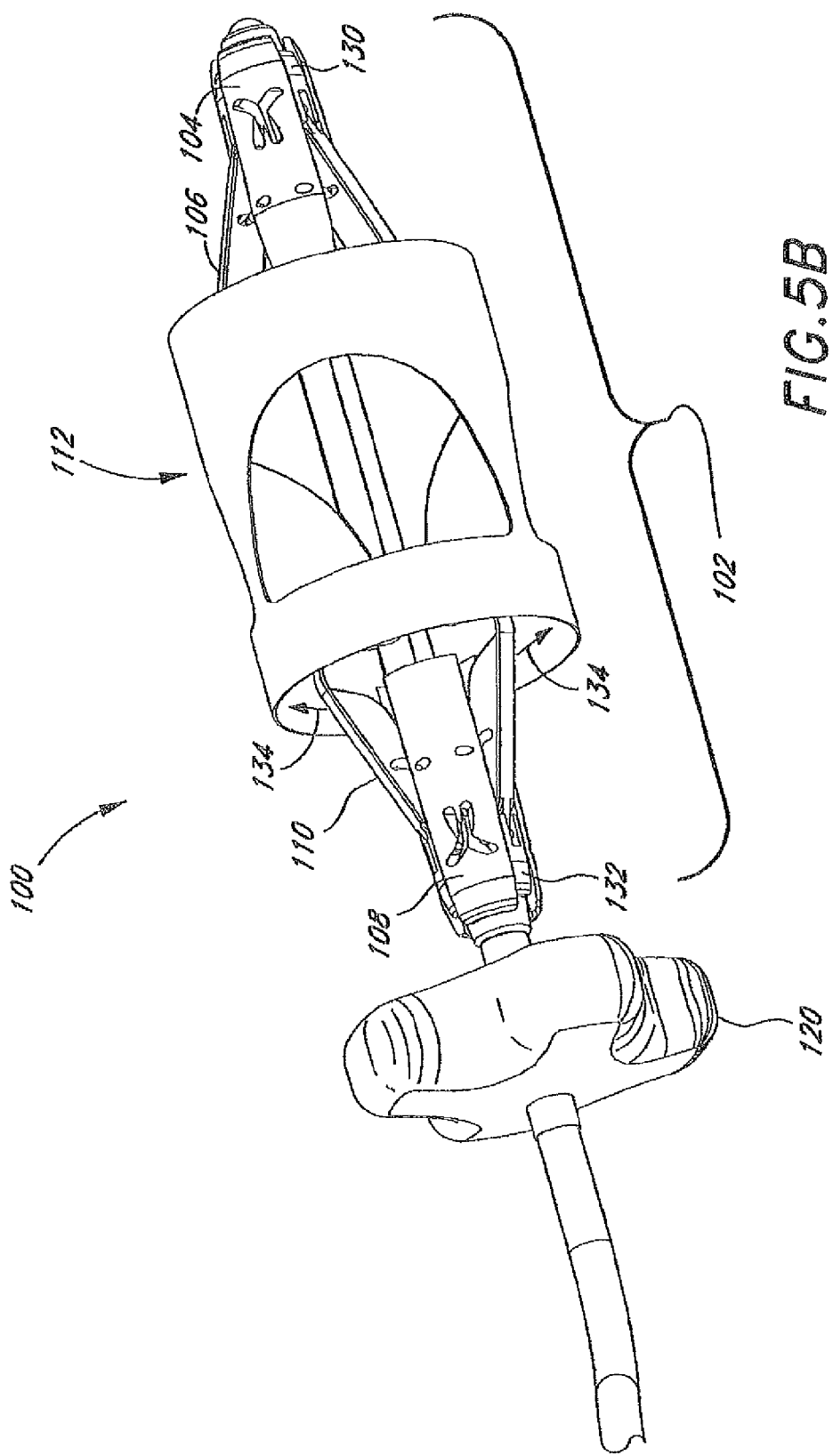

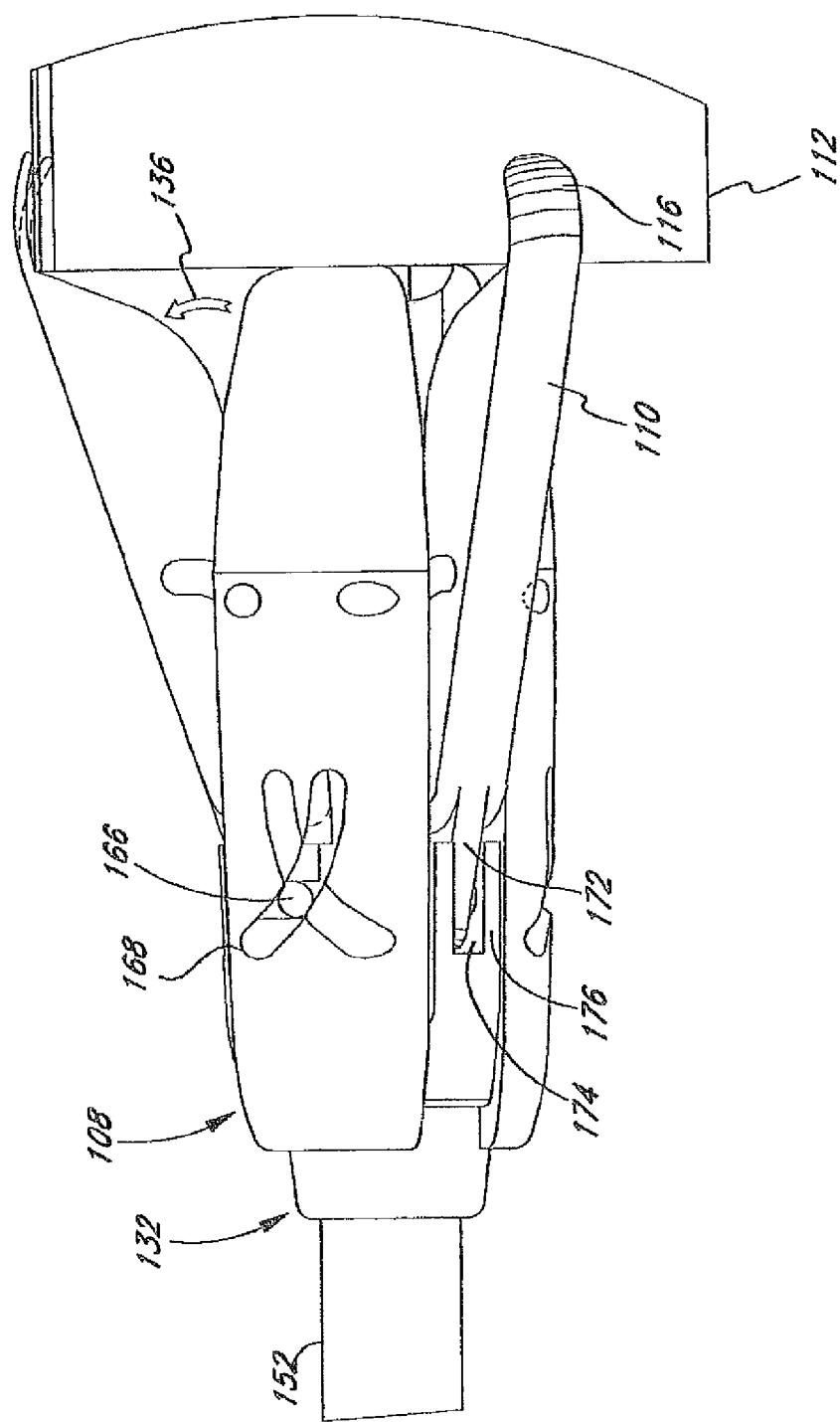

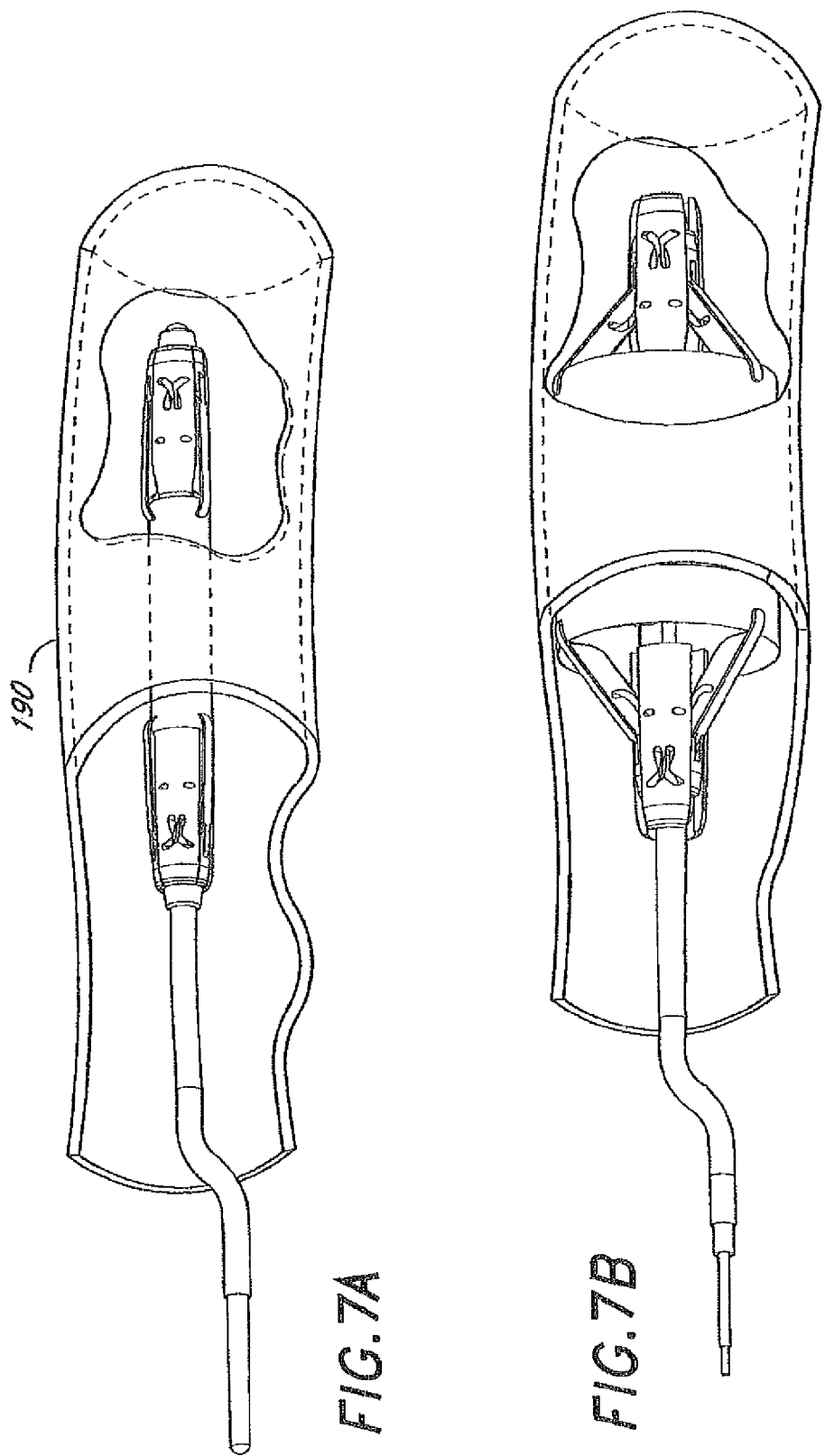

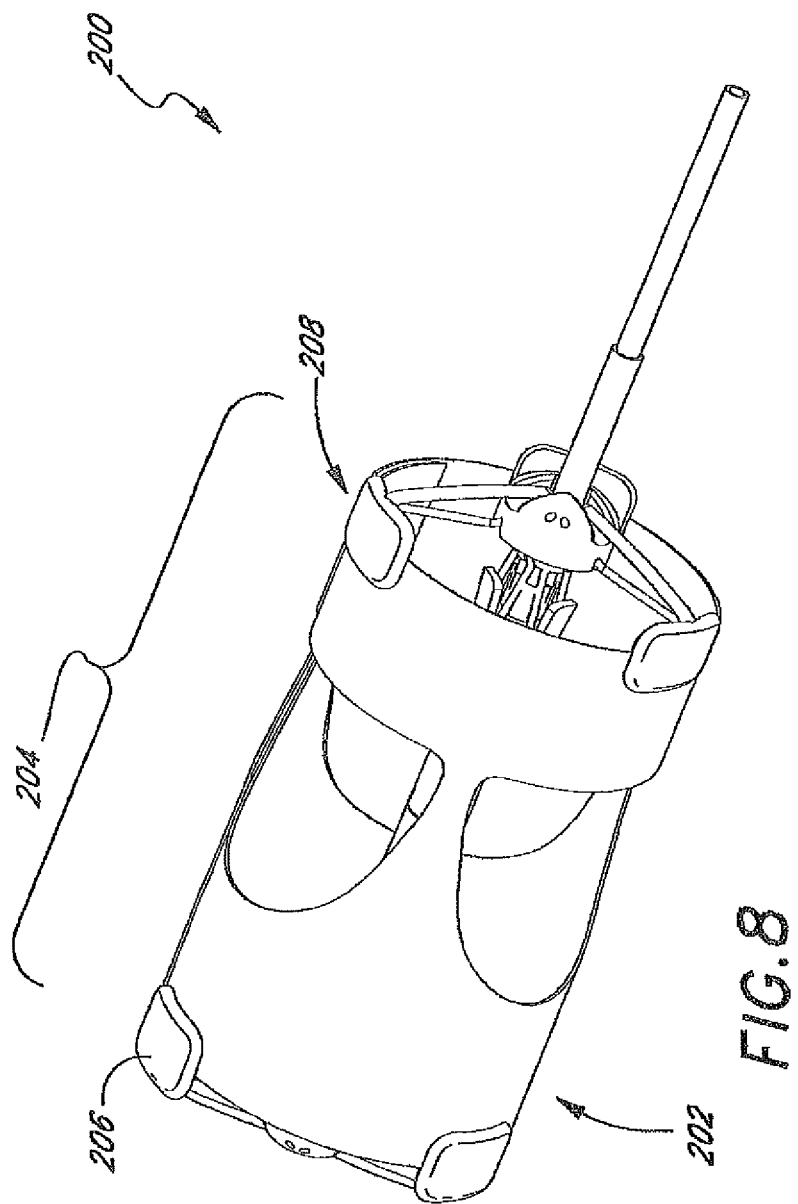

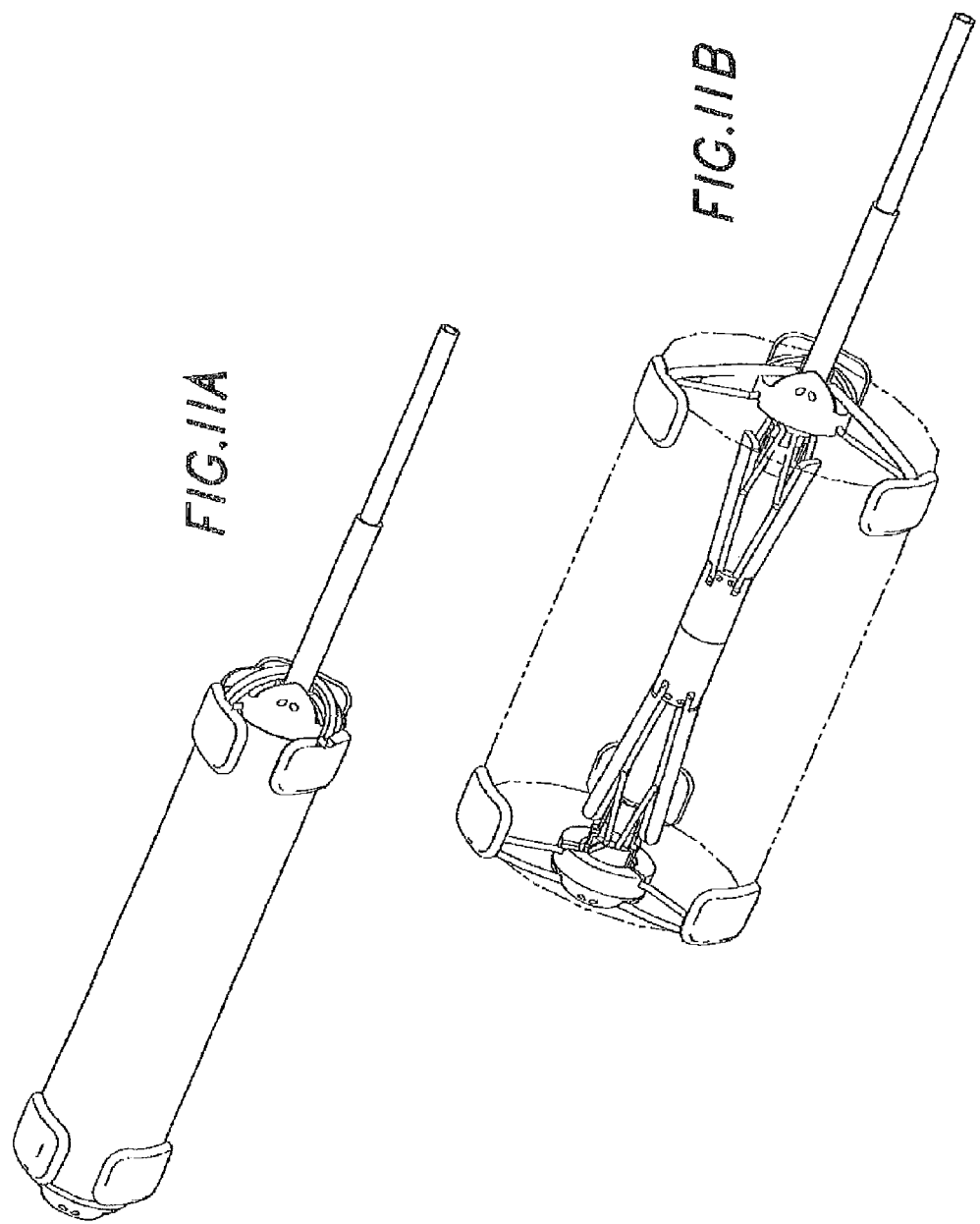

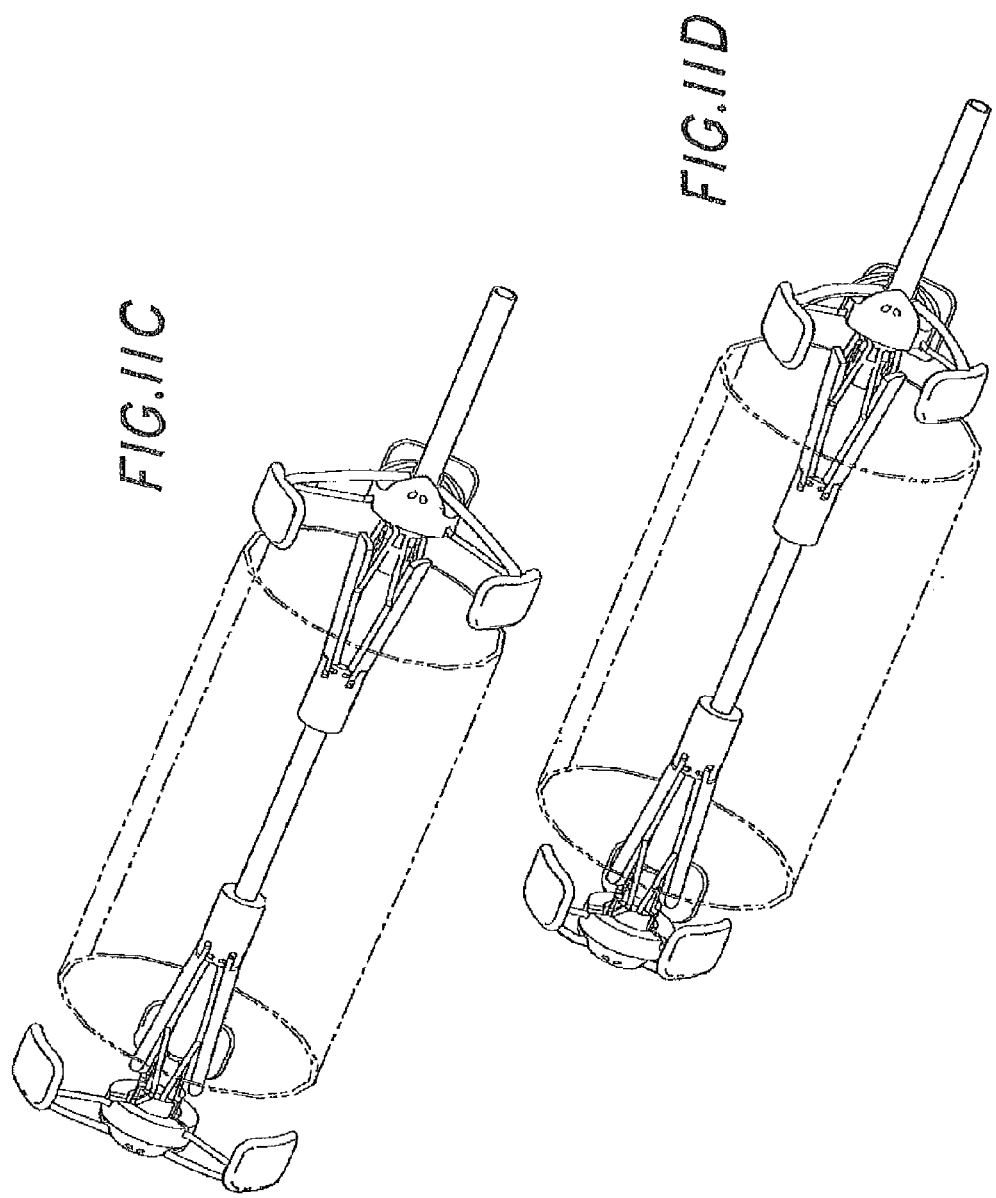

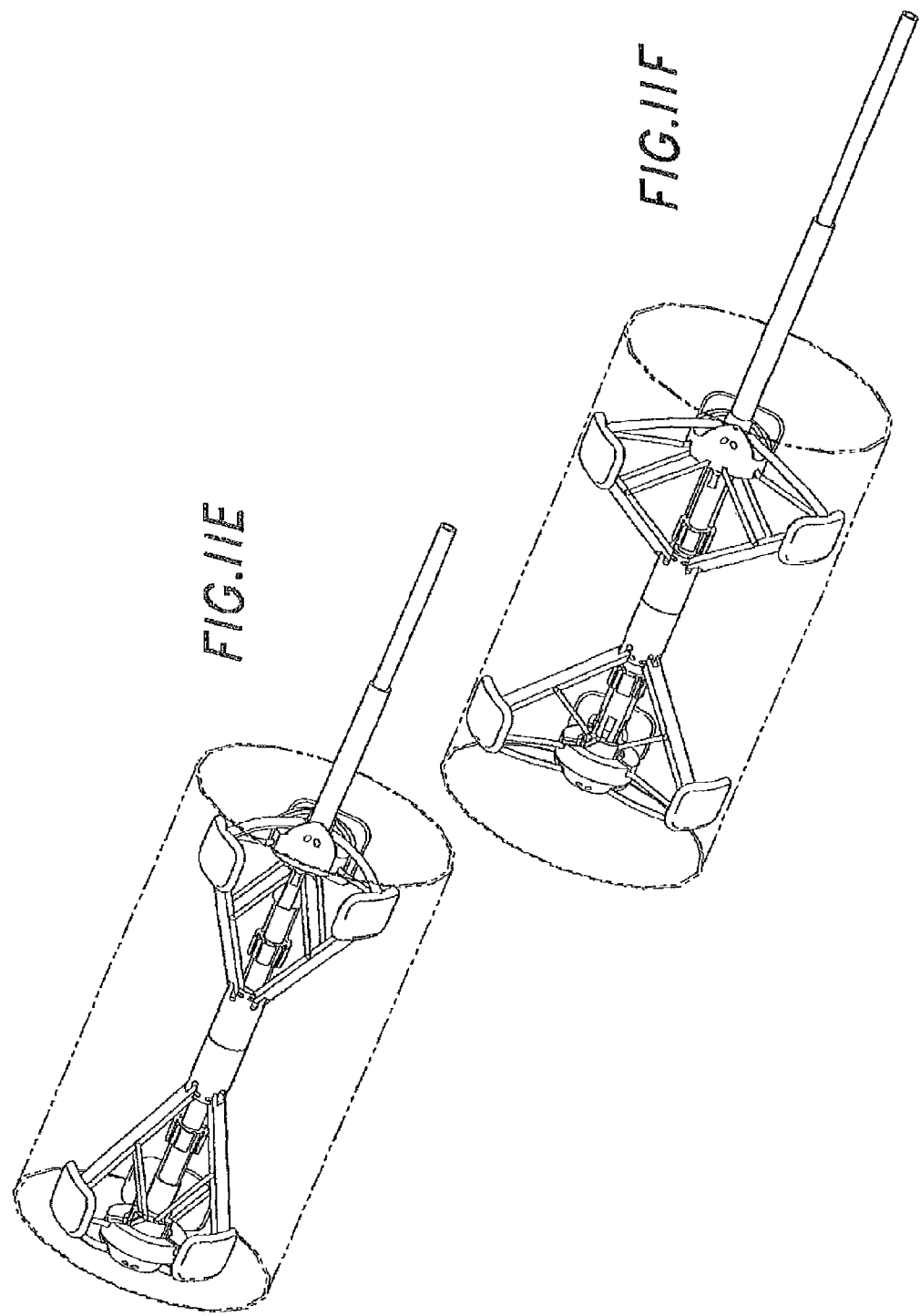

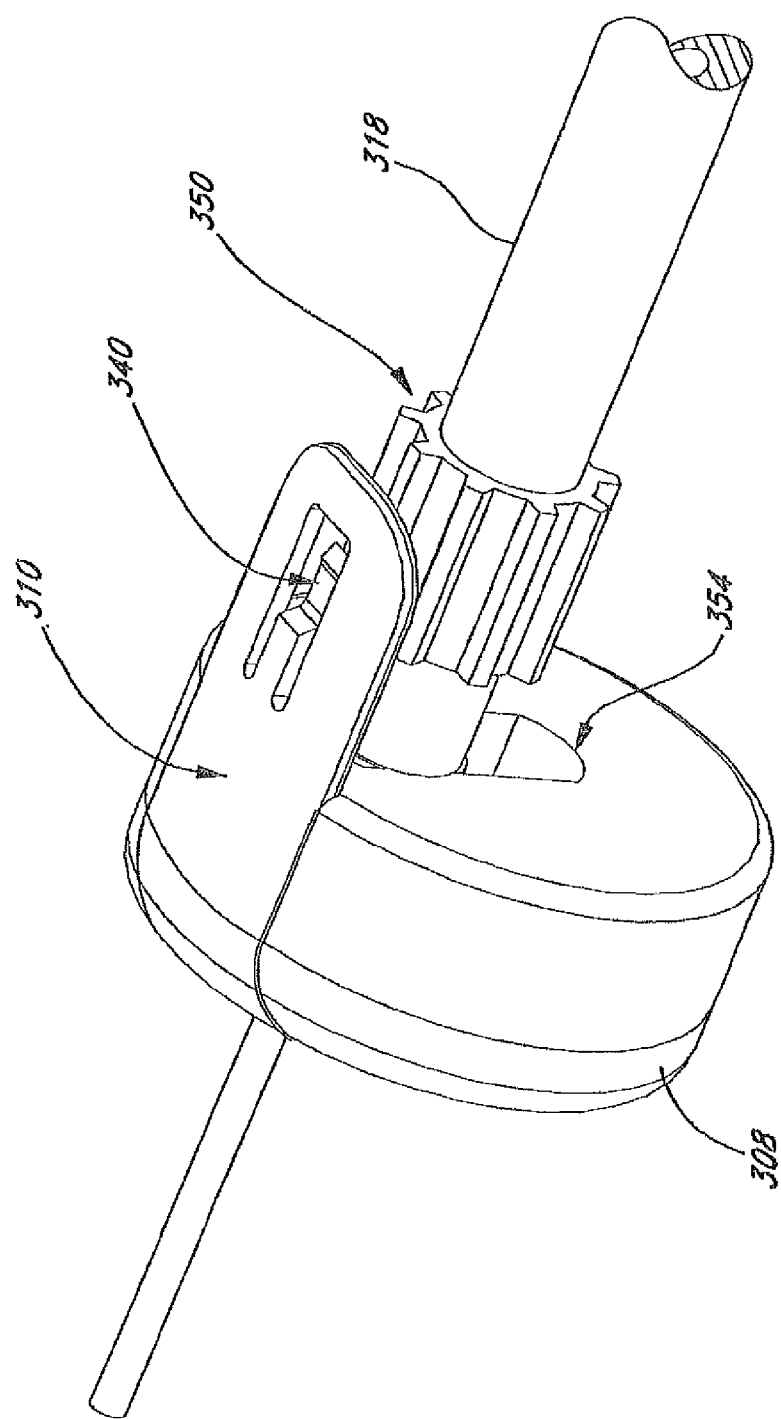

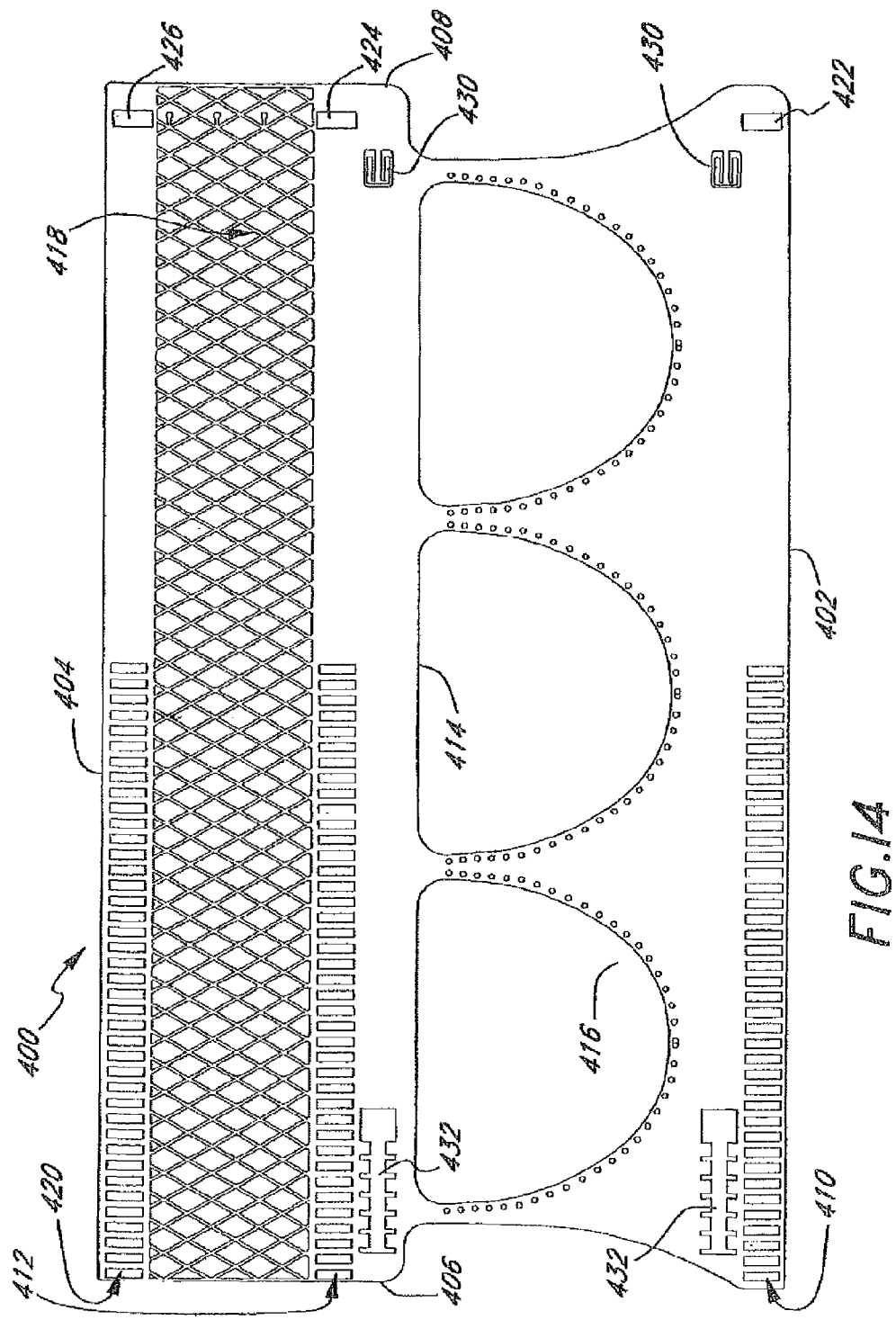

METHODS AND APPARATUSES FOR DEPLOYING MINIMALLY-INVASIVE HEART VALVES

CROSS-REFERENCE TO RELATED APPLICATIONS

This application is a continuation of U.S. application Ser. No. 13/350,730, filed Jan. 13, 2012, now U.S. Pat. No. 9,452,046, which is a continuation of U.S. application Ser. No. 12/488,480, filed Jun. 19, 2009, now U.S. Pat. No. 8,740,975, which is a continuation for of U.S. application Ser. No. 09/951,701, filed Sep. 13, 2001, now U.S. Pat. No. 7,556,646, the disclosures all of which are incorporated by reference in their entireties.

FIELD OF THE INVENTION

The present invention relates generally to medical devices and particularly to methods and devices for deploying expandable heart valve prostheses especially for use in minimally-invasive surgeries.

BACKGROUND OF THE INVENTION

Prosthetic heart valves are used to replace damaged or diseased heart valves. In vertebrate animals, the heart is a hollow muscular organ having four pumping chambers: the left and right atria and the left and right ventricles, each provided with its own one-way valve. The natural heart valves are identified as the aortic, mitral (or bicuspid), tricuspid and pulmonary valves. Prosthetic heart valves can be used to replace any of these naturally occurring valves.

Where replacement of a heart valve is indicated, the dysfunctional valve is typically cut out and replaced with either a mechanical valve or a tissue valve. Tissue valves are often preferred over mechanical valves because they typically do not require long-term treatment with anticoagulants. The most common tissue valves are constructed with whole porcine (pig) valves, or with separate leaflets cut from bovine (cow) pericardium. Although so-called stentless valves, comprising a section of porcine aorta along with the valve, are available, the most widely used valves include some form of stent or synthetic leaflet support. Typically, a wireform having alternating arcuate cusps and upstanding commissures supports the leaflets within the valve, in combination with an annular stent and a sewing ring. The alternating cusps and commissures mimic the natural contour of leaflet attachment.

A conventional heart valve replacement surgery involves accessing the heart in the patient's thoracic cavity through a longitudinal incision in the chest. For example, a median sternotomy requires cutting through the sternum and forcing the two opposing halves of the rib cage to be spread apart, allowing access to the thoracic cavity and heart within. The patient is then placed on cardiopulmonary bypass which involves stopping the heart to permit access to the internal chambers. Such open heart surgery is particularly invasive and involves a lengthy and difficult recovery period.

Recently, a great amount of research has been done to reduce the trauma and risk associated with conventional open heart valve replacement surgery. In particular, the field of minimally invasive surgery (MIS) has exploded since the early to mid-1990's, with devices now being available to enable valve replacements without opening the chest cavity. MIS heart valve replacement surgery still typically requires bypass, but the excision of the native valve and implantation of the prosthetic valve are accomplished via elongated tubes (catheters or cannulas), with the help of endoscopes and other such visualization techniques. Some examples of recent MIS heart valves are shown in U.S. Pat. No. 5,411,552 to Anderson, et al., U.S. Pat. No. 5,980,570 to Simpson, U.S. Pat. No. 5,984,959 to Robertson, et al., PCT Publication No. 00/047139 to Garrison, et al., and PCT Publication No. WO 99/334142 to Vesely.

The typical MIS valve of the prior art includes a directly radially expanding stent that is initially compressed for delivery through a cannula, and is then expanded at the site of implantation after removing the constraint of the cannula. The expansion is accomplished using an internal balloon catheter around which the stent is compressed.

Despite various delivery systems for conventional MIS valves, there remains a need for a delivery system that more reliably controls the expansion of new MIS valves.

SUMMARY OF THE INVENTION

In accordance with a preferred embodiment, the present invention provides a system for delivering and deploying an expandable prosthetic heart valve, comprising a catheter shaft having a proximal end and a distal end and a lumen therethrough extending along an axis. The heart valve deployment mechanism extends axially from the distal end of the catheter shaft, and includes spaced apart proximal and distal deployment members. An actuating shaft extends through the lumen of the catheter shaft and operates to actuate at least one of the proximal and distal deployment members. The deployment members may be radially movable and comprise fingers each pivoted at one end thereof to the deployment mechanism. There are desirably at least two proximal deployment fingers and at least two distal deployment fingers, wherein the deployment fingers are axially movable. The deployment members may be radially movable and there are two of the actuating shafts. A first actuating shaft operates to radially displace the proximal deployment members and a second actuating shaft operates to radially displace the distal deployment members, wherein the first and second actuating shafts are concentrically disposed to slide with respect one another.

In one embodiment the deployment mechanism comprises a proximal collet with respect to which the proximal deployment members pivot, and a distal collet with respect to which the distal deployment members pivot, wherein the proximal collet and distal collet are relatively axially movable. A first actuating shaft extends within a cavity in the proximal collet and a first driver attaches thereto that acts upon the proximal deployment members to pivot them with respect to the proximal collet. A second actuating shaft extends through the first actuating shaft and into a cavity in the distal collet and a second driver attaches thereto that acts upon the distal deployment members to pivot them with respect to the distal collet.

There are various ways to actuate the deployment members. First, each deployment member may pivot about a point that is fixed with respect to the associate collet and includes structure that engages cooperating structure on the associated driver, wherein axial movement of the driver rotates the structure about the pivot point, thus rotating the deployment member. Alternatively, each deployment member has a pin fixed with respect thereto that is received within a corresponding slot in the associated driver, and each collet includes a plurality of pins fixed with respect thereto that are received within corresponding slots in the associated deployment members. In the alternative configuration, axial movement of the driver displaces the pins fixed with respect to the deployment members and causes the deployment members to pivot outward due to a camming action of the deployment member slots over the collet pins.

In a still further embodiment, each deployment member may comprise a pad that is coupled to a respective proximal and distal end cap disposed along the catheter shaft, the pads being radially displaceable with respect to the associated end cap, wherein the proximal and distal end caps are axially movable with respect to each other. There may be two of the actuating shafts, each shaft controlling a plurality of flexible tongs having column strength that extend between one of the end caps and attach to the associated pads, wherein axial movement of each shaft shortens or lengthens the radial extent of the flexible tongs controlled thereby so as to radially displace the attached pads.

Still further, each deployment member may comprise a gear that engages a gear track on the heart valve.

The system preferably includes a stabilization balloon on the catheter shaft proximal to the deployment mechanism and sized to expand and contact a surrounding vessel adjacent the site of implantation. The stabilization balloon may be shaped so as to permit blood flow past it in its expanded configuration, such as with multiple outwardly extending lobes.

The heart valve deployment mechanism may be a modular unit coupled to the distal ends of the catheter shaft and actuating shaft.

In another aspect of the invention, a system for delivering and deploying a self-expandable prosthetic heart valve to a site of implantation is provided. The system comprises a catheter for advancing the heart valve in a contracted configuration to the site of implantation; means on the catheter for permitting the heart valve to self-expand from its contracted configuration to an initial expanded configuration in contact with the surrounding site of implantation; and means for regulating the rate of self-expansion of the heart valve. The system may also include means for expanding the heart valve from its initial expanded configuration to a final expanded configuration, such as a balloon. Alternatively, the means for expanding the heart valve from its initial expanded configuration to a final expanded configuration may be the same as the means for regulating the rate of self-expansion of the heart valve.

The means for expanding the heart valve from its initial expanded configuration to its final expanded configuration and the means for regulating the rate of self-expansion of the heart valve may comprise a gear mechanism that engages both the distal and proximal ends of the heart valve. If the heart valve is of the rolled type having multiple wound layers, the gear mechanism may have a gear shaft that engages an inner layer of the spirally wound heart valve and a retaining bar that engages an outer layer of the spirally wound heart valve, wherein the distance between the gear shaft and retaining bar is adjustable.

Another aspect of the invention is a system for delivering and deploying an expandable prosthetic heart valve to a site of implantation, comprising a catheter for advancing the heart valve in a contracted configuration to the site of implantation, and a stabilization device provided on the catheter sized to expand and contact a surrounding vessel adjacent the site of implantation. The system also has means on the catheter distal to the stabilization device for expanding the heart valve from its contracted configuration to an initial expanded configuration in contact with the surrounding site of implantation. The stabilization device may be a balloon shaped so as to permit blood flow past it in its expanded configuration, such as for example with multiple outwardly extending lobes.

A method for delivering and deploying a self-expandable prosthetic heart valve to a site of implantation is also provided by the present invention. The method comprises:
advancing the heart valve in a contracted configuration to the site of implantation;
permitting the heart valve to self-expand from its contracted configuration to an initial expanded configuration in contact with the surrounding site of implantation; and
regulating the rate of self-expansion of the heart valve.

In the preferred method, the step of advancing the heart valve in a contracted configuration to the site of implantation comprises providing a heart valve deployment mechanism that in one operating mode maintains the heart valve in the contracted configuration, and in another operating mode regulates the rate of self-expansion of the heart valve. The heart valve deployment mechanism may have a plurality of proximal deployment members that engage a proximal end of the valve, and a plurality of distal deployment members that engage a distal end of the valve, and wherein coordinated radial movement of the proximal and distal deployment members regulates the rate of self-expansion of the heart valve. Alternatively, the heart valve deployment mechanism includes a gear shaft having a plurality of gear teeth that engage a gear track provided on the heart valve, wherein the rate of self-expansion of the heart valve is regulated by regulating the rotational speed of the gear shaft.

The preferred method further includes expanding the heart valve from its initial expanded configuration to a final expanded configuration. Also, a catheter-based valve deployment mechanism may be provided having deployment members that both regulate the rate of self-expansion of the heart valve and expand the heart valve from its initial expanded configuration to its final expanded configuration. Alternatively, a catheter-based valve deployment mechanism may be provided having deployment members that regulate the rate of self-expansion of the heart valve, and an inflation balloon expands the heart valve from its initial expanded configuration to its final expanded configuration. In the latter case, the valve inflation balloon is separate from the deployment mechanism and is introduced into the valve after at least a partial expansion thereof. The method further desirably includes stabilizing the heart valve in its contracted configuration adjacent the site of implantation prior to permitting the heart valve to self-expand. The step of stabilizing the heart valve may involve inflating a stabilization balloon, and also permitting blood flow past the inflated stabilization balloon.

A further understanding of the nature and advantages of the invention will become apparent by reference to the remaining portions of the specification and drawings.

BRIEF DESCRIPTION OF THE DRAWINGS

FIG. 5B is a perspective view as in FIG. 5A illustrating a final step of deployment of the heart valve;

FIG. 6A is an enlarged elevational view of a portion of the distal end of the delivery and deployment system of FIG. 4;

FIGS. 7A-7F are perspective views showing a number of steps in the delivery and deployment of an expandable heart valve using the system of FIG. 4;

FIG. 8 is a perspective view of the distal end of a second alternative delivery and deployment system of the present invention showing a heart valve in its expanded configuration;

FIGS. 11A-11F are perspective views showing a number of steps in the delivery and deployment of an expandable heart valve using the system of FIG. 8;

FIG. 13 is an enlarged perspective view of a portion of the delivery and deployment system of FIG. 12 shown without the heart valve; and FIG. 14 is a plan view of a stent of an expandable heart valve of the present invention for use with the third alternative delivery and deployment system as seen in FIG. 12.

DESCRIPTION OF THE PREFERRED EMBODIMENTS

Figure 1:
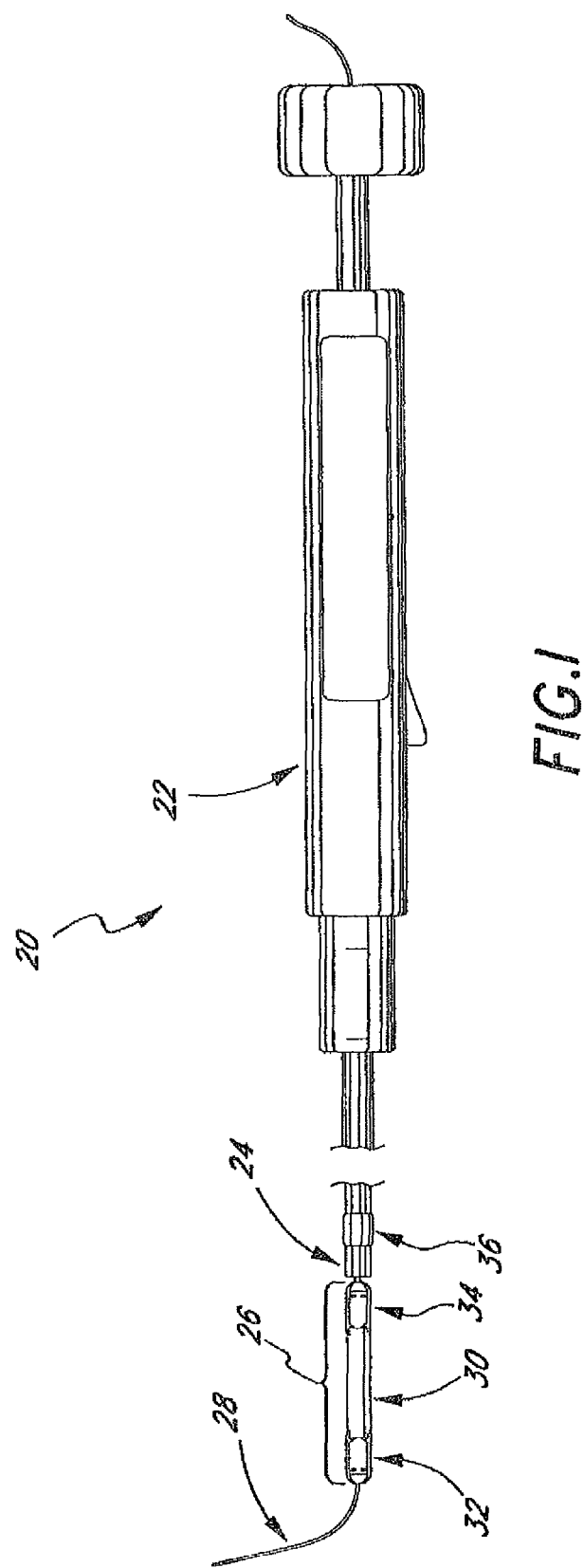
FIG. 1 is an elevational view of an exemplary expandable heart valve delivery and deployment system of the present invention with a catheter shaft shown broken so as to illustrate the main components thereof.

The present invention discloses a number of expandable heart valves for implantation in a host annulus, or host tissue adjacent the annulus. The valves may be implanted in any of the four valve positions within the heart, but are more likely to be used in replacing the aortic or mitral valves because of the more frequent need for such surgery in these positions. The patient may be placed on cardiopulmonary bypass or not, depending on the needs of the patient.

A number of expandable prosthetic heart valves are disclosed in co-pending U.S. application Ser. No. 09/815, 521 that are initially rolled into a tight spiral to be passed through a catheter or other tube and then unfurled or unrolled at the implantation site, typically a valve annulus. These will be denoted "rolled heart valves" and comprise one- or two-piece sheet-like stent bodies with a plurality of leaflet-forming membranes incorporated therein. Various materials are suitable for the stent body, although certain nickel-titanium alloys are preferred for their super-elasticity and biocompatibility. Likewise, various materials may be used as the membranes, including biological tissue such as bovine pericardium or synthetic materials. It should also be noted that specific stent body configurations disclosed herein or in U.S. application Ser. No. 09/815,521 are not to be considered limiting, and various construction details may be modified within the scope of the invention. For example, the number and configuration of lockout tabs (to be described below) may be varied.

As a general introduction, the heart valves in a first, spirally-wound or contracted configuration are delivered through a tube such as a percutaneously-placed catheter or shorter chest cannula and expelled from the end of the tube in the approximate implantation location. The heart valve is then expanded into a second, unwound or expanded configuration that engages the native host tissue, such as the target valve annulus. Depending on the native valve being replaced, the prosthetic heart valve may have varying axial lengths. For example, in the aortic position, an outflow portion of the valve may extend upward into and even flare out and contact the aorta to better stabilize the commissure regions of the valve. In other words, the particular design of the valve may depend on the target valve location.

The present invention is particularly adapted for delivering and deploying self-expandable rolled heart valves, although those of skill in the art will recognize that certain embodiments may be adapted for deploying plastically deformable rolled heart valves. Self-expandable stents in general are known, typically constructed of a tubular metal lattice that has a normal, relaxed diameter and is compressed for insertion into a vein or artery. Upon expulsion from the end of a catheter, the tubular metal lattice expands to its original larger diameter in contact with the vessel wall. It is important to note that there is no regulation of the self-expansion of the stent, as the tube reliably assumes its larger shape.

A number of embodiments of the present invention will now be described with reference to the attached drawings. It should be understood that the various elements of any one particular embodiment may be utilized in one or more of the other embodiments, and thus combinations thereof are within the scope of the appended claims.

FIG. 1 illustrates an exemplary system 20 for delivering and deploying an expandable heart valve. The main elements of the system 20 include a proximal operating handle 22, a catheter shaft 24 extending distally from the handle and shown broken to fit on the page, a heart valve deployment mechanism 26, and a guidewire 28 typically extending entirely through the system. The expandable heart valve 30 is seen held in a contracted configuration between a distal collet body 32 and a proximal collet body 34 of the deployment mechanism 26. The system may further include a stabilization balloon 36 provided on the catheter shaft 24 just proximal the deployment mechanism 26.

Prior to describing the exemplary deployment mechanism 26, and alternative mechanisms, in greater detail, an overview of the techniques for using the system 20 is appropriate. For this discussion, it will be assumed that the heart valve 30 will be implanted in the aortic position.

Prior to introduction of the distal end of the system 20 into the patient, the expandable heart valve 30 is selected based on a measurement of the aortic annulus. Various sizing methodology are available, a discussion of which is outside the scope of the present invention. The selected heart valve 30 may be initially wound into a tight spiral in its storage container, or it may be stored expanded and then wound into its contracted configuration just prior to use. For this purpose, co-pending U.S. application Ser. No. 09/945,392, entitled Container and Method for Storing and Delivering Minimally-Invasive Heart Valves, filed Aug. 30, 2001, now U.S. Pat. No. 6,723,122, which is expressly incorporated herein, may be used. That application discloses a system for storing and then automatically converting an expandable valve into its contracted shape while still in the storage container. Additionally, the valve 30 may be stored along with the deployment mechanism 26 as a modular unit. In that case, the deployment mechanism 26 and valve 30 may be snapped onto or otherwise coupled with the distal end of the catheter shaft 24. This enables one operating handle 22 and catheter shaft 24 to be used with a number of different valve/deployment mechanism units. After those of skill in the art have an understanding of the various control or actuation shafts/cables described herein, the coupling structure should be relatively straightforward, and thus a detailed explanation will not be provided.

The guidewire 28 is first inserted into a peripheral artery, such as the femoral or carotid, using known techniques, and advanced through the ascending aorta into the left ventricle. The catheter shaft 24 with the deployment mechanism 26 on its leading or distal end is then passed over the guidewire 28, possibly with the assistance of an intermediate sized obturator, and into the peripheral vessel via the well-known Seldinger method. The operator then advances and positions the deployment mechanism 26 in proximity to the implantation site, in this case the aortic annulus, using visualization devices such as radiopaque markers on the deployment mechanism 26 or heart valve 30, or an endoscope. Advancement of the deployment mechanism 26 involves simply pushing the entire catheter shaft 24 along the guidewire 28 using the handle 22. Once the valve 30 is properly positioned, the operator expands the stabilization balloon 36 into contact with the surrounding aorta. In this manner, the heart valve 30 is both axially and radially anchored with respect to the surrounding annulus to facilitate proper engagement therewith. The stabilization balloon 36 may be shaped to permit blood flow in its expanded configuration for beating heart surgeries.

Expansion of the heart valve 30 may be accomplished in various ways, as will be described in greater detail below. Operation of the deployment mechanism 26 involves manipulation of cables, shaft, or other elongated devices passing from the operating handle 22 through the catheter shaft 24. These elongated devices may be utilized to transfer axial (push/pull) forces or rotational torque initiated in the handle 22 to various elements of the deployment mechanism 26. The present application will not focus on specific mechanisms in the handle 22 for initiating the forces on the cables or shafts passing through the catheter shaft 24, as numerous such apparatuses are known in the art.

Figure 2:
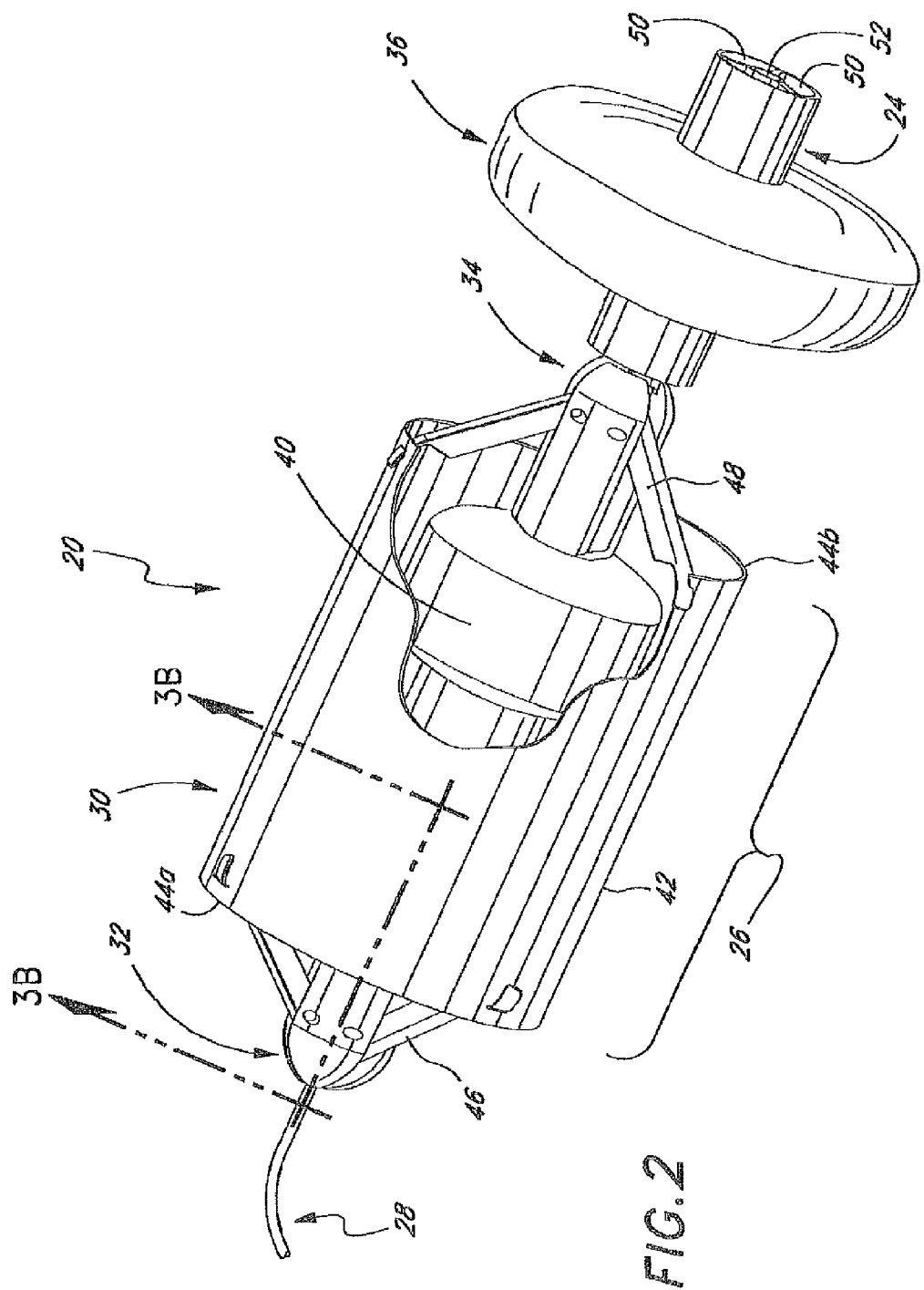
FIG. 2 is a perspective view of the distal end of the delivery system of FIG. 1 showing a heart valve in its expanded configuration.

Now with reference to FIG. 2, the distal end of the delivery and deployment system 20 is illustrated with the deployment mechanism 26 holding the generally tubular heart valve 30. The heart valve 30 is shown in an expanded configuration with a portion cut away to illustrate a lockout balloon 40 therewithin. The heart valve 30 has a rolled configuration and includes a generally sheet-like stent body 42 that unwinds from a tight spiral into an expanded tube having a distal end 44a and a proximal end 44b. A plurality of distal deployment members or fingers 46 extending proximally from the distal collet body 32 engage the valve body distal end 44a, while a plurality of proximal deployment fingers 48 extending distal from the proximal collet body 34 engage the valve body proximal end 44b. It should be noted that various features of the heart valve 30, such as the valve leaflets, are not illustrated for clarity.

The inflated stabilization balloon 36 is shown having generally a disk-shape, although other shapes are contemplated, such as a lobed-shape to permit blood flow, as will be described below. A cross-section of the catheter shaft 24 illustrates a plurality of outer lumens 50 surrounding a central lumen 52. The lumens 50 may be used for inflating the balloon 36, 40, or for passing fluid or the devices therethrough. The central lumen 52 is typically used for passage of the cables or shafts for operating the deployment mechanism 26.

Figure 3A:
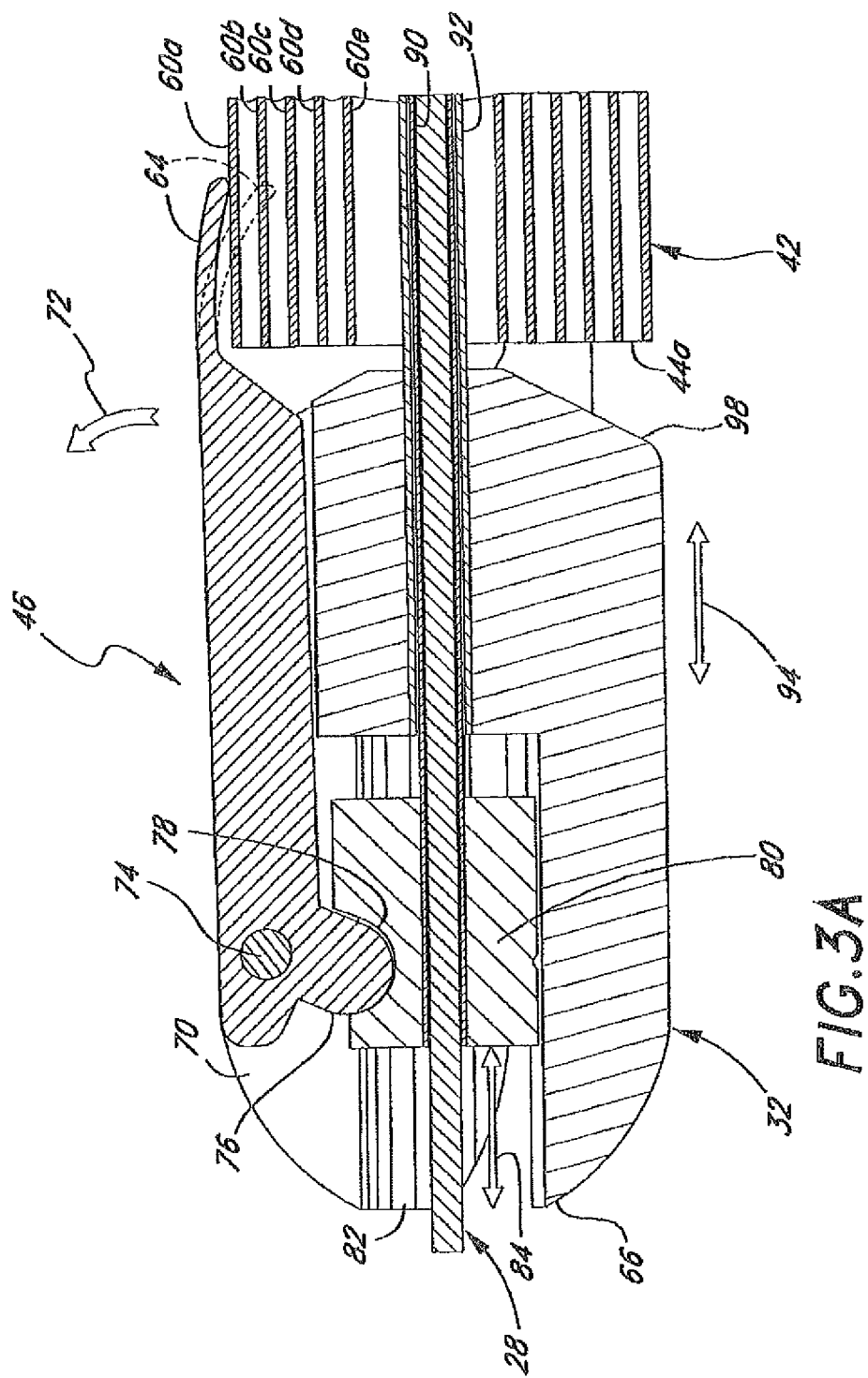
FIG. 3A is a longitudinal sectional view through a portion of the distal end of the delivery and deployment system of FIG. 1 illustrating part of a mechanism for controlling the expansion of a heart valve, which is shown in its contracted configuration.
Figure 3B:
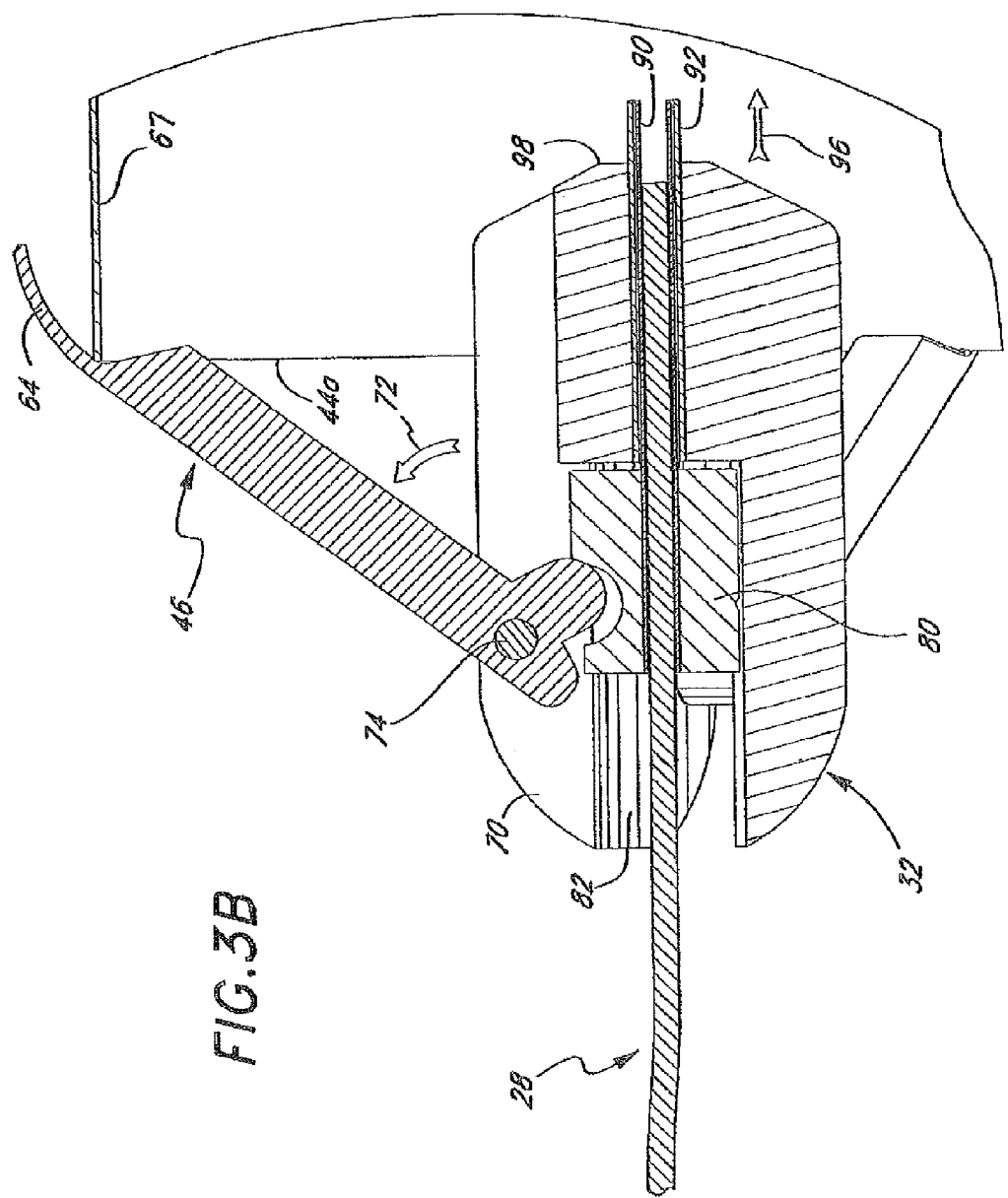
FIG. 3B is a longitudinal sectional view as in FIG. 3A showing the heart valve expanded.

FIGS. 3A and 3B illustrate in cross-section the details of the distal end of the deployment mechanism 26, and specifically the distal collet body 32. FIG. 3A shows the heart valve body 42 in its contracted configuration with multiple spirally wound layers 60a-60e, while FIG. 3B shows the valve body 42 in its expanded configuration having only one layer 62. The distal deployment fingers 46 each possesses a flexible claw 64 that directly engages the outer layer 60a of the valve body 42. The flexible claw 64 has an initial curved set indicated in dashed line that applies a radially inward spring force to the valve body 42. When in the position of FIG. 3A, the claw 64 flexes outward into a generally linear configuration, and helps prevent damage to the valve body by the fingers 46, 48. At least two of the fingers 46, 48 on each end, and preferably three or more, retain the valve body 42 in its spirally wound or contracted configuration during delivery through the vascular system to the site of implantation. It should be noted also that the distal collet body 32 has a rounded, generally bullet-shaped nose 66 that facilitates introduction into and passage through the vascular system.

As seen in FIG. 3A, each of the fingers 46 initially resides within an axial channel 70 formed in the collet body 32 and pivots outward in a radial plane in the direction of arrow 72 about a collet pin 74 fixed in the collet body across the channel. In the radially inward configuration of FIG. 3A, the fingers 46 are recessed within the channels 70 to present a low introduction profile for the deployment mechanism 26. Each of the fingers 46 includes a lever 76 that engages a depression 78 within a distal driver 80. The driver 80 reciprocates axially within a cavity 82 formed within the distal collet body 32, as indicated by the double-headed movement arrow 84. From the position shown, proximal movement of the driver 80 with respect to the collet body 32 acts on the lever 76 to pivot the finger 46 outward in the direction of arrow 72. The lever 76 is shown rounded so as to easily slide within the similarly shaped though concave depression 78. Of course, other arrangements for coupling axial movement of the distal driver 80 to rotational movement of the finger 46 are possible.

A distal driver shaft 90 extends over the guidewire 28 to be fixed within a bore of the distal driver 80. Likewise, the distal collet shaft 92 is concentrically disposed about the distal driver shaft 90 and is fixed within a bore of the distal collet body 32. All these elements are thus coaxial about the guide wire 28. Axial movement of the shafts 90, 92 causes axial movement of the driver 80 and collet body 32, respectively. Collet movement is indicated by the double-headed arrow 94. In the initial delivery configuration of FIG. 3A, the collet body 32 is positioned distally from the distal end 44a of the valve body 42.

In operation of the deployment mechanism 26 of FIG. 2, as best seen in FIG. 3B, the distal driver 80 is displaced within the cavity 82 by relative movement of the distal driver shaft 90 and distal collet shaft 92, and interaction between the lever 76 and depression 78 causes outward pivoting motion of the finger 46. Because the valve body 42 is annealed into its expanded configuration, outward pivoting of the fingers 46 permits expansion thereof.

Therefore, the valve body 42 converts from its spirally wound configuration with multiple spirally-wound layers 60a, 60e as seen in FIG. 3A, to the expanded configuration of FIG. 3B having the single layer 62. During this expansion, contact between the flexible claws 64 and the outer layer 60a of the valve body 42 is maintained by controlling the relative movement between the distal driver 80 and the distal collet body 32. This contact between the claws 64 and valve body 42 regulates the speed or rate of expansion of the valve body, thus preventing any mis-alignment problems. That is, because of the provision of both the distal collet body 32 and proximal collet body 34, and associated fingers 46 and 48, the rate of expansion of both the distal end 44a and proximal end 44b of the valve body 42 can be equilibrated. Because both ends of the valve body 42 expand at the same rate, the valve forms a tube father than potentially expanding into a partial cone shape.

It is important to note that during transition of the valve body 42 from its contracted to its expanded configuration, the distal collet body 32 moves in a proximal direction with respect to the valve body 42 as indicated by the movement arrow 96. The reader will note the different relative positions of the proximal end of the collet body 32 with respect to the distal end 44a of the valve body 42 in FIGS. 3A and 3B. This collet body 32 movement results from relative movement of the distal collet shaft 92 with respect to the valve body 42, which body position is determined by the position of the proximal fingers 48, or by a supplemental shaft (not shown) coupled to the operating handle 22. Because of the proximal collet body 32 movement with respect to the valve body 42, the flexible claws 64 maintain the same axial position with respect to the valve body 42 during outward pivoting of the fingers 46. That is, outward pivoting of the fingers 46 causes both radially outward and distal axial movement of the claws 64 with respect to collet pin 74, and the axial component of movement must be accommodated by movement of the collet body 32 or else the claws 64 would disengage the valve body 42. The distal collet body 32 includes a frusto-conical proximal end 98 that facilitates displacement of the collet body into the partially unwound valve body 42, and prevents binding therebetween.

The valve body 42 expands outward under regulation of the fingers 46, 48 until it contacts the surrounding host tissue. The valve body 42 has an annealed shape such that its relaxed configuration is open, with its inner and outer side edges being spaced apart. As such, the valve body 42 will continue to expand until it contacts the surrounding tissue, as long as the final tubular size of the valve is larger than the site of implantation. Therefore, proper sizing of the valve is extremely important.

Once the valve body 42 contacts the surrounding tissue, it has reached its initial expanded state. At this stage, the deployment fingers 46, 48 remain outwardly pivoted but are moved apart by relative axial movement of the collet bodies 32, 34 away from each other so as to disengage the claws 64 from the distal and proximal ends 44a, 44b of the valve body 42. Once disengaged from the valve, the fingers 46, 48 may be retracted into their respective channels 70. Subsequently, inflation of the lockout balloon 40 (FIG. 2) further expands the valve body 42 into more secure engagement with the surrounding tissue until lockout features on the valve body engage and secure the valve body in its final expanded configuration. These lockout features are fully described in co-pending U.S. application Ser. No. 09/815,521, which disclosure is hereby expressly incorporated by reference.

The lockout balloon 40 resides initially in the catheter shaft 24 or even outside of the body during the first phase of expansion of the valve body 42. Because the valve body 42 advances through the vasculature in a relatively tight spiral so as to minimize its radial profile for minimally invasive surgeries, the lockout balloon 40 is preferably not positioned in the middle thereof. Of course, this constraint is necessary only when the insertion space is limited, and if the surgery is open heart or otherwise not so space-limited then the balloon 40 may indeed be initially positioned inside and delivered along with the valve. In the preferred minimally invasive deployment, however, the balloon must be introduced within the valve body 42 after at least a partial expansion or unwinding thereof. Typically, the valve body 42 expands into its initial expanded configuration in contact with the surrounding tissue before the lockout balloon 40 advances into its position as seen in FIG. 2, although the balloon may be advanced into the valve as soon as a sufficient space in the middle of the valve opens up.

The lockout balloon 40 preferably has a shape with enlarged ends and a connecting middle portion, much like a dumbbell. In this manner, the balloon acts on the proximal and distal ends of the valve body 42, without contacting a middle portion where the leaflets of the valve are located. Of course, other arrangements of balloon are possible, as are multiple lockout balloons.

After the valve body 42 is fully implanted, the lockout balloon 40 is deflated and the catheter shaft 24 withdrawn from the body along the guide wire 28. The proximal collet body 34 also has a bullet-shaped proximal end to facilitate this removal through the vasculature.

Figure 4:
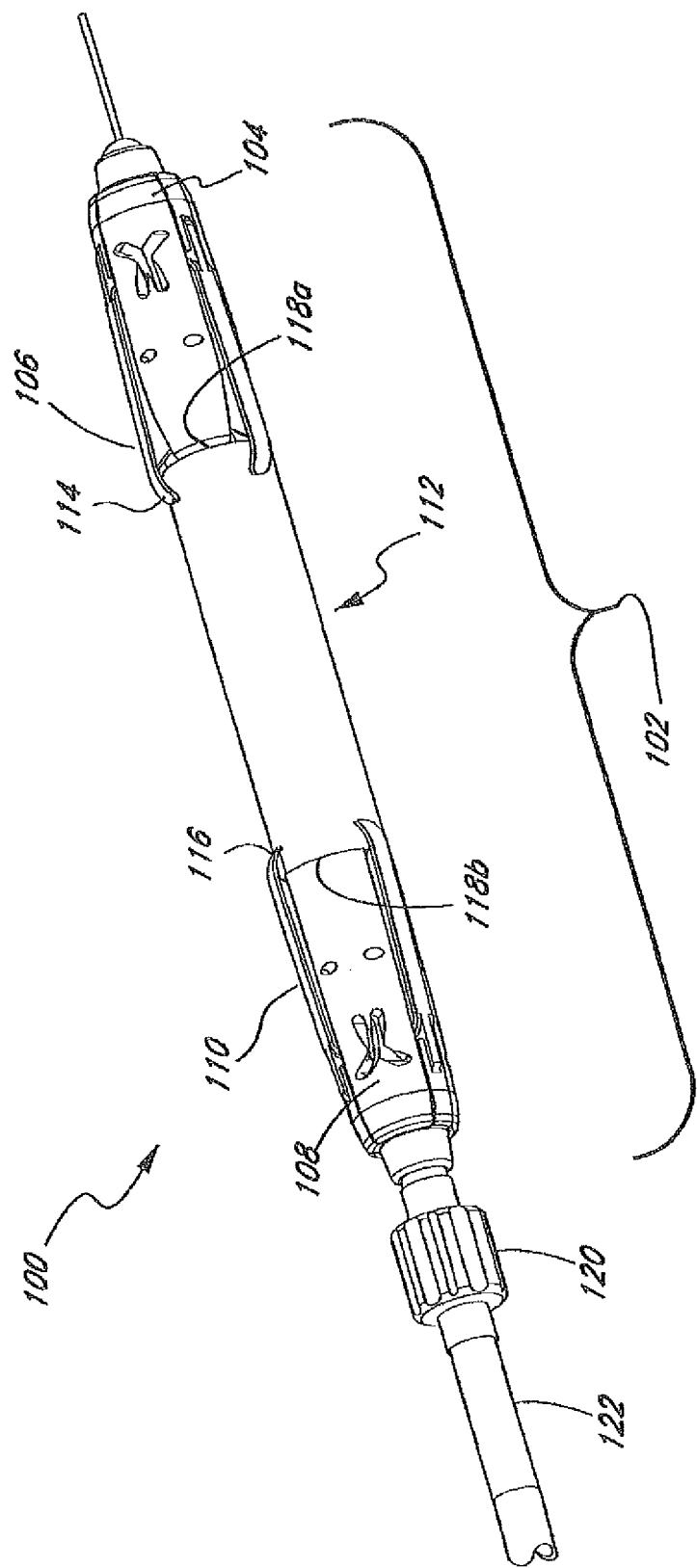
FIG. 4 is a perspective view of the distal end of an alternative heart valve delivery and deployment system of the present invention showing a heart valve in its contracted configuration.

FIGS. 4-6B illustrate the distal end of an alternative expandable heart valve delivery and deployment system 100 of the present invention that is in many ways similar to the first-described embodiment of FIGS. 1-3B. Namely, as seen in FIG. 4, the system 100 includes a deployment mechanism 102 having a distal collet 104 with a plurality of deployment members or fingers 106, and a proximal collet 108 having a plurality of deployment members or fingers 110. The deployment fingers 106, 110 engage respective ends of a self-expandable heart valve 112, which is shown in its contracted configuration. As in the earlier embodiment, the deployment fingers 106, 110 enable regulated self-expansion of the heart valve 112 to ensure the valve expands to the correct tubular shape. Although there are a number of constructional differences between the two embodiments, the main functional difference pertains to the manner in which flexible claws 114, 116 of the deployment fingers 106, 110 are maintained in particular axial locations with respect to the distal and proximal ends 118a, 118b, respectively, of the valve 112. In the first-described embodiment, the collets 32, 34 were axially displaced along with the drivers 80, thus necessitating axial movement and coordination of four different shafts, while in the embodiment of FIGS. 4-6B movement of only two shafts are needed. This modification will become clear below.

Figure 5A:
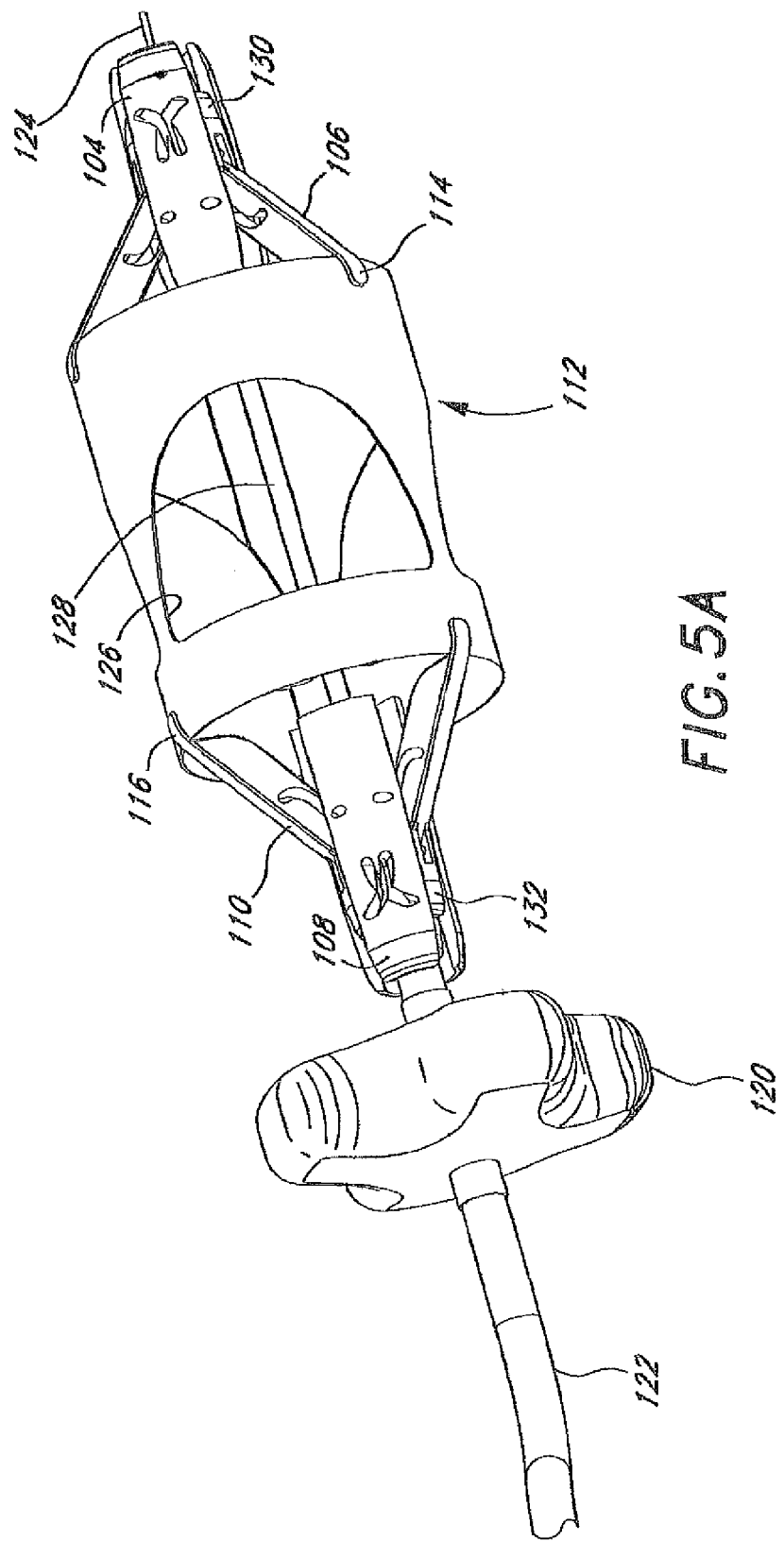
FIG. 5A is a perspective view of the delivery and deployment system of FIG. 4 showing the heart valve in its expanded configuration and an inflated stabilization balloon.

FIG. 4 illustrates a stabilization balloon 120 in its folded or deflated configuration just proximal to proximal collet 108. FIG. 5A shows the stabilization balloon 120 inflated and assuming a four-lobed star shape. The entire distal end of the system 100 is positioned at the distal end of a catheter shaft 122 and travels over a guide wire 124. The stabilization balloon 120 is sized to expand and contact a surrounding vessel adjacent the site of implantation, such as the ascending aorta. The star shape of the stabilization balloon 120 permits blood flow in the expanded configuration of the balloon for beating heart surgeries, though of course other balloon shapes could be used. Furthermore, devices other than a balloon for stabilizing the distal end of the system 100 may be utilized. For example, a mechanical expanding structure having struts or a wire matrix may work equally as well as a balloon and also permit blood flow therethrough. Therefore, the term stabilization device refers to all of the above variants.

FIG. 5A also illustrates the heart valve 112 in its initial expanded configuration such that a plurality of leaflet mounting windows 126 are visible. In this case, the leaflets are not shown for clarity so as to expose a distal collet shaft 128 extending through the middle of the valve between the proximal and distal collets 104, 108. The heart valve 112 is permitted to expand into the shape shown in FIG. 5A by outward pivoting of the respective flexible claws 114, 116 of the deployment fingers 106, 110. This pivoting occurs by proximal movement of a distal driver 130 with respect to the distal collet 104, and distal movement of a proximal driver 132 with respect to the proximal collet 104. The change in the relative positions of the drivers 130, 132 and collets 104, 108 may be seen by comparison of FIG. 4 and FIG. 5A.

FIG. 5B shows the deployment mechanism 102 during a valve deployment phase that converts the valve 112 from its initial expanded configuration to a final expanded or locked out configuration. The deployment fingers 106, 110 have been displaced so that they reside within the tubular valve 112 and are then in a position to be once again pivoted outward, as indicated by the arrows 134, into contact with the valve. In this case, therefore, a separate lockout balloon within the valve 112, such as balloon 40 in FIG. 1, may not be necessary, unless the additional expansion force is required. A full sequence of operation of the deployment system 100 will be described below with respect to FIGS. 7A-7F after an exemplary construction of the system is explained.

Figure 6B:
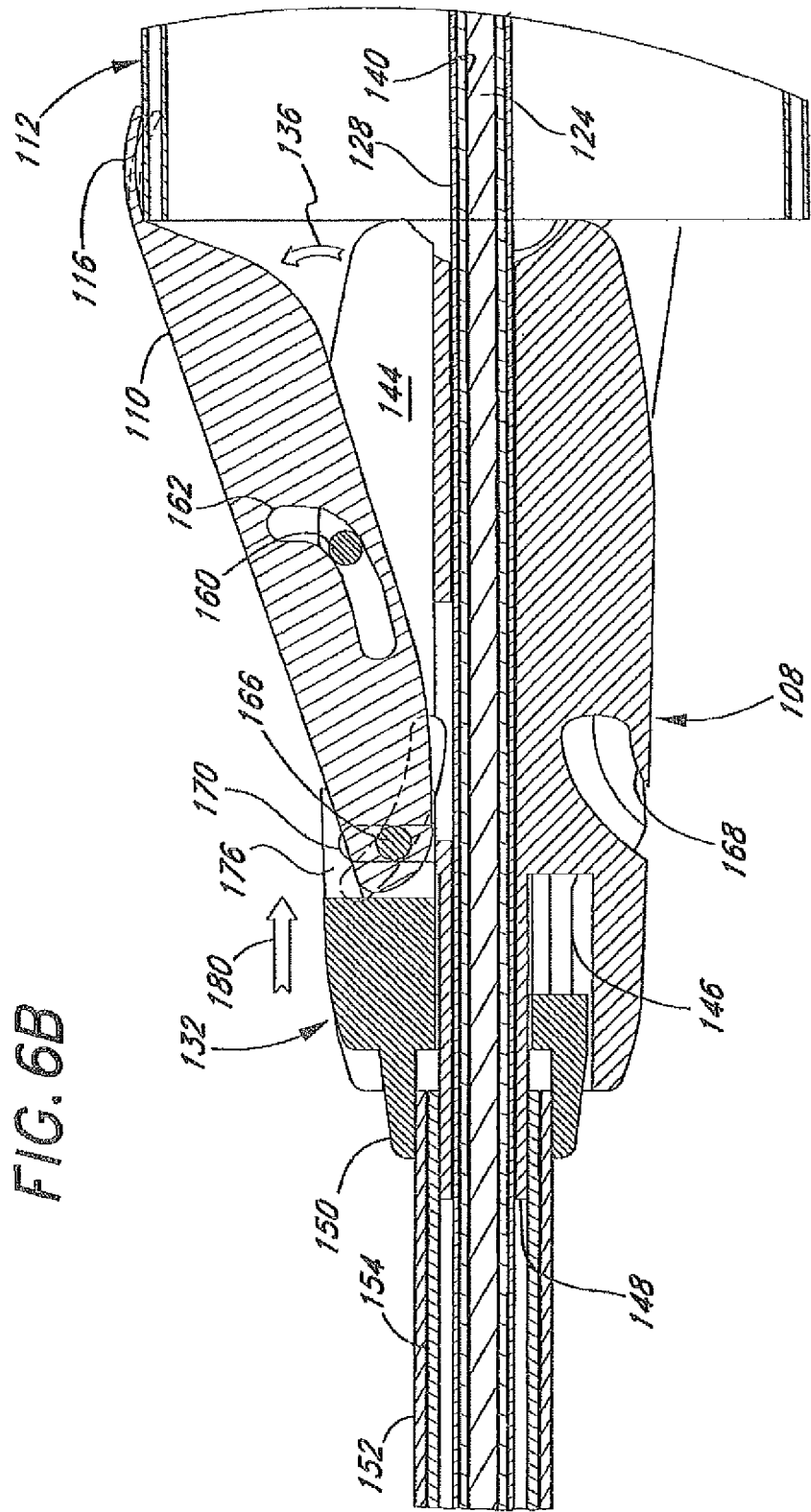
FIG. 6B is an enlarged longitudinal sectional view of the portion of the distal end of the delivery and deployment system seen in FIG. 6A.

FIGS. 6A and 6B illustrate, in elevational and sectional views, respectively, the proximal end of the deployment system 102 with the fingers 110 pivoted open to an intermediate position during the stage of self-expansion of the valve 112 from its contracted configuration to its initial expanded configuration. The flexible claws 116 are shown in contact with the exterior of the valve body 112, with their curved set shown in phantom. The direction of movement of the fingers 110 is indicated in both views by the movement arrow 136.

With specific reference to FIG. 6B, the collet 108 includes a central through bore (not numbered) that slidingly receives the distal collet shaft 128. The distal collet shaft 128, in turn, slidingly receives a distal driver shaft 140, which directly travels over the guidewire 124. Each of the deployment fingers 110 resides within an axial collet channel 144 that extends from the distal end of the collet 108 into proximity with a cavity 146 located on the proximal end. The proximal driver 132 reciprocates within the cavity 146 and includes a through bore (not numbered) that slides over a tubular boss 148 extending proximally from the collet 108. The driver 132 includes a proximal tubular flange 150 that closely receives and is fixed with respect to a proximal driver shaft 152. A proximal collet shaft 154 mounts to the exterior of the tubular boss 148 of the collet 108, and is adapted to slide within the proximal driver shaft 152. By virtue of the four shafts 128, 140, 152, and 154, the collets 104, 108 and drivers 130, 132 may be axially displaced with respect to one another.

The proximal collet 108 carries a plurality of collet pins 116 that are fixed across an approximate midpoint of each of the collet channels 144 and are received within curved finger cam slots 162. As mentioned previously, two, and preferably three fingers 110 are required for reliable regulation of the self expansion of the valve 112, and there are an equivalent number of collet channels 144 and pins 160. The finger cam slots 162 are disposed in the middle of each finger 110, and the finger also carries a pin 166 fixed to its proximal end. As seen best in FIG. 6A, each finger pin 166 travels along a curvilinear collet cam slot 168. The finger pins 166 are each also constrained by a linear driver travel slot 170 that is best seen in FIG. 6B. With reference again to FIG. 6A each finger 110 includes a flange portion 172 that is received in a driver channel 174 formed between bifurcated walls 176 of the proximal driver 132. The driver travel slot 170 is thus formed in both walls 176.

Movement of the various components of the proximal end of the deployment mechanism 102 is depicted in FIG. 6B. The outward pivoting motion of the finger 110 is indicated by arrow 136. The outward finger movement is accomplished by distal movement of the finger 110 with respect to the collet pin 160 which travels from the upper right end of the finger cam slot 162 to the lower left end. Because the collet pin 160 is fixed with respect to the collet 108, the finger 110 moves outward by the caroming action of the pin 160 within the slot 162. Distal movement of the finger 110 is caused by movement in the distal direction of the driver 132 with respect to the collet 108, as indicated by arrow 180, due to the engagement between the driver travel slot 170 and the finger pin 166. As the finger pin 166 moves in the distal direction, it travels along the curvilinear collet cam slot 168. The linear driver travel slot 170 accommodates radially inward movement of the finger pin 166 in this regard.

The shapes of the finger cam slot 162 and collet cam slot 168 are designed such that the claw 116 at the distal end of the finger 110 moves radially outward but remains in the same axial position. Furthermore, this movement of the finger 110 is accomplished by maintaining the proximal collet 108 in a fixed relationship with respect to the valve body 112, while only displacing the proximal driver 132 in a distal direction, indicated by arrow 180. As such, only the proximal driver cable 152 need be displaced. In the same manner, only the distal driver shaft 140 need be displaced with respect to the distal collet shaft 128 to actuate the distal deployment fingers 106 (FIG. 4). Indeed, the distal and proximal collets 104, 108 remain stationary with respect to the valve 112 while the distal and proximal drivers 130, 132 are displaced toward one another. Likewise, the fingers 106, 110 are retracted radially inwardly by opposite movement of the drivers 130, 132.

Figure 7C:
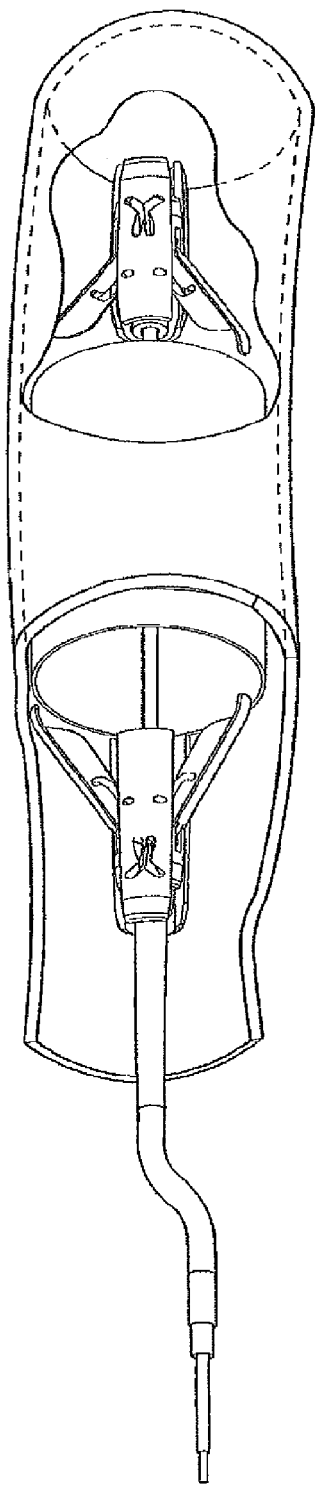

A sequence of steps in the delivery and deployment of a heart valve utilizing the deployment mechanism 102 of FIG. 4 is seen in FIGS. 7A-7F. FIG. 7A shows the deployment mechanism and heart valve in their radially contracted configurations such that the entire assembly resembles an elongated bullet for easy passage through the vasculature of the patient, which is indicated by a generic vessel 190. After reaching the site of implantation, the valve 112 is permitted to self expanded under control of the deployment fingers. Namely, the proximal and distal drivers move axially toward one another permitting the fingers to pivot open which in turn allows the spirally wound expandable heart valve to unwind. The heart valve unwinds at a controlled rate into its initial expanded configuration in contact with the surrounding tissue, as explained above.

Figure 7D:
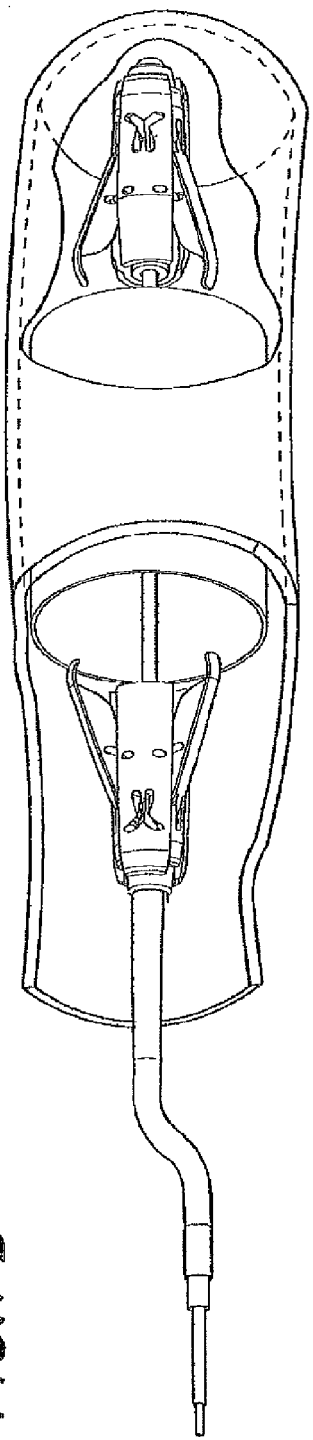
Figure 7E:
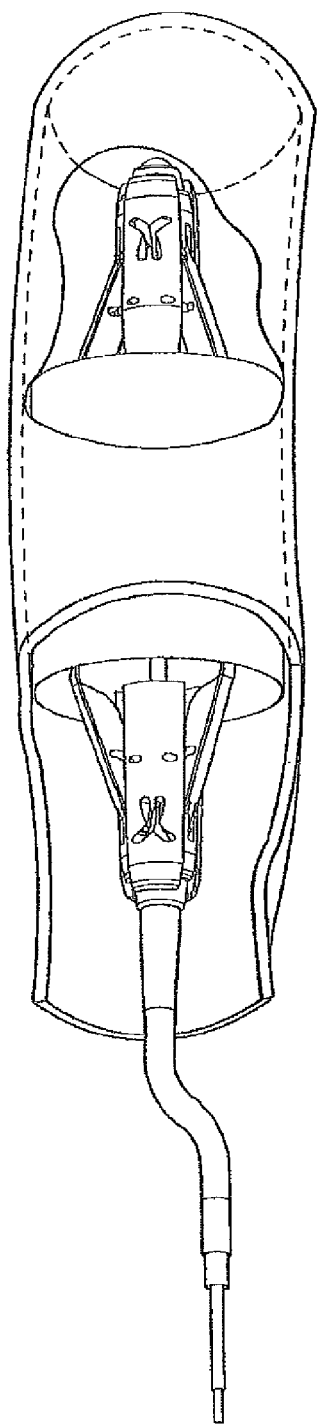
Figure 7F:
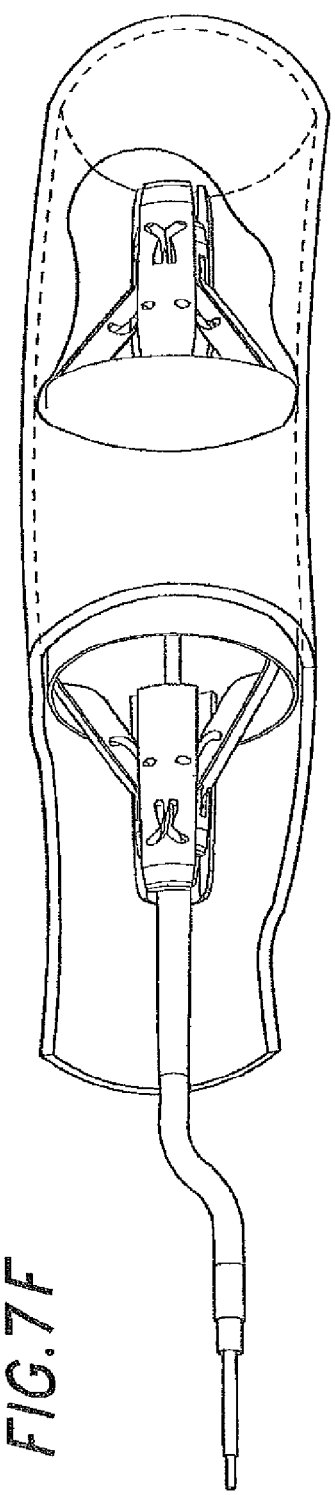

Now with reference to FIG. 7C, the distal and proximal collets are axially displaced away from one another so that the claws at the end of the fingers release from the ends of the heart valve. Subsequently, as seen in FIG. 7D, movement of the proximal and distal drivers away from one another and with respect to the associated collets retracts the fingers inward a slight amount. FIG. 7E shows the deployment mechanism after the collets have been axially advanced toward one another such that the claws at the end of the fingers are disposed within the heart valve. In a final deployment step, as seen in FIG. 7F, the proximal and distal drivers are again advanced toward one another and with respect to the stationary collets so that the fingers pivot outward into contact with the interior of the valve. The fingers force the valve outward against the surrounding vessel and into its locked position. The deployment mechanism is then removed from the body by retracting the deployment fingers and pulling the catheter along the guide wire.

Figure 9:
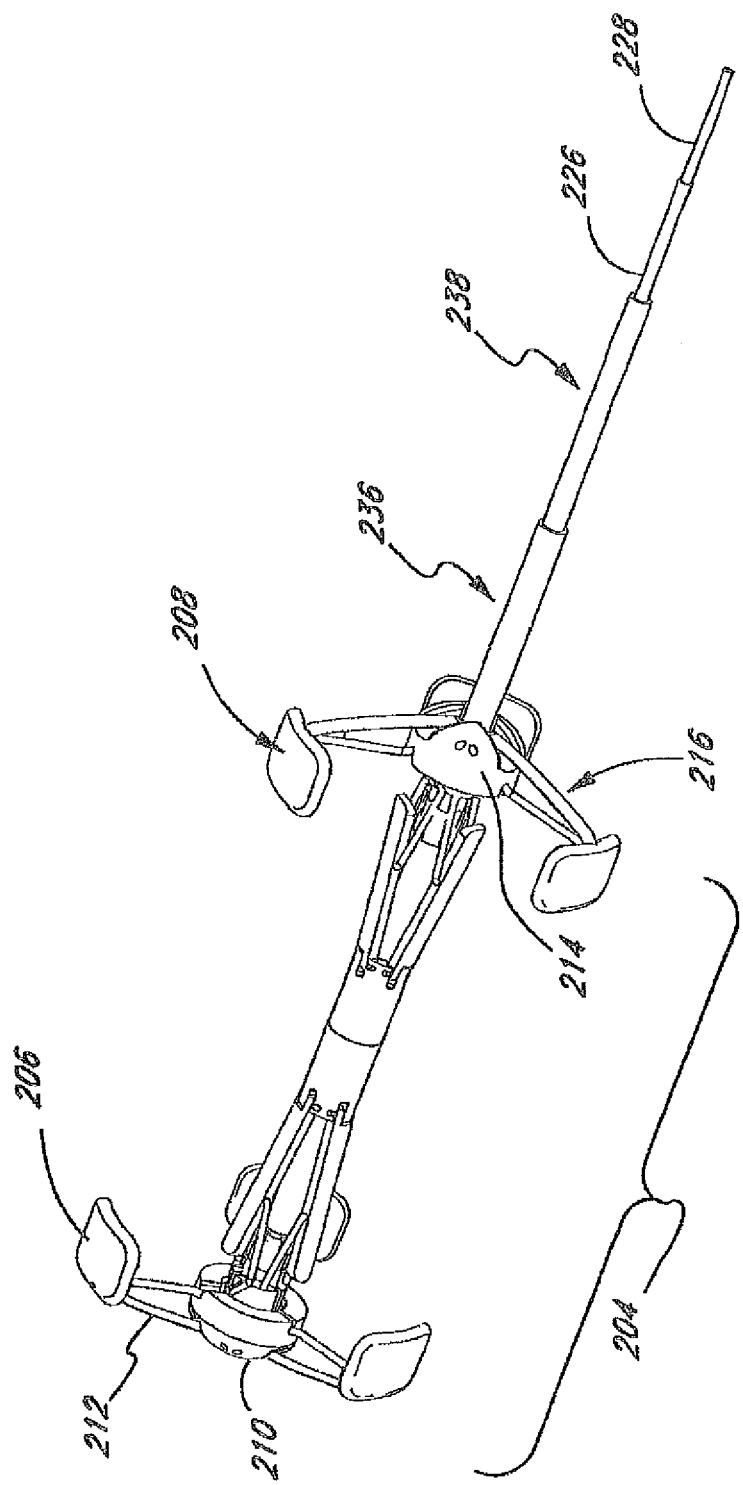
FIG. 9 is a perspective view of the distal end of the second alternative delivery and deployment system shown as in FIG. 8 without the heart valve.

FIGS. 8-10A illustrates a second alternative heart valve delivery and deployment system 200 of the present invention that operates in much the same manner as the first two embodiments described above, although without pivoting deployment members. FIG. 8 illustrates the distal end of the system 200 with an expandable heart valve 202 held therewithin in its initial expanded configuration. FIG. 9 illustrates the distal end of the system 200 in the same configuration but without the heart valve. The system 200 includes a valve deployment mechanism 204 having a plurality of distal deployment pads 206 and a plurality of proximal deployment pads 208 that engage the valve 202. The pads 206, 208 are shown in FIG. 8 on the exterior of the valve that enables the aforementioned control of the valve self-expansion. The pads 206, 208 are desirably relatively rigid and have rounded edges and/or are otherwise coated with a material that prevents damage to the valve 202.

With specific reference to FIG. 9, each of the distal pads 206 (preferably three) couples to a distal end cap 210 via a tension spring 212. Likewise, each of the proximal pads 208 (preferably three) couples to a proximal end cap 214 via a tension spring 216. The springs 212, 216 exert radially inward forces on each of the pads 206, 208. The end caps 210, 214 are mounted on separately movable shafts such that their axial spacing may be varied.

Figure 10:
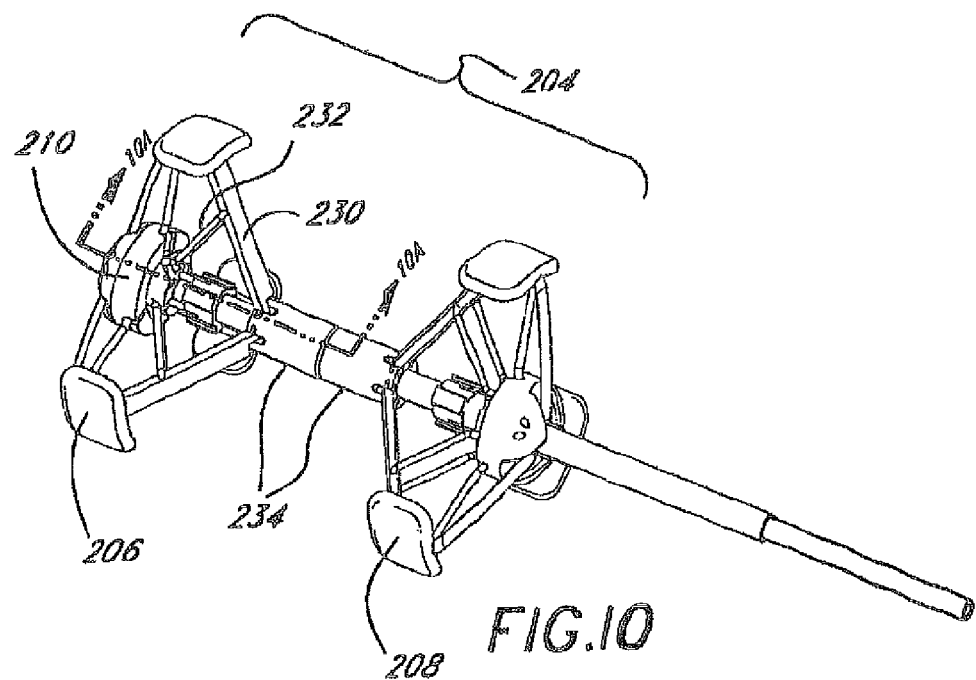
FIG. 10 is a perspective view of the distal end of the delivery and deployment system of FIG. 8 shown in a mode of operation that expands the heart valve outward into a locked position.
Figure 10A:
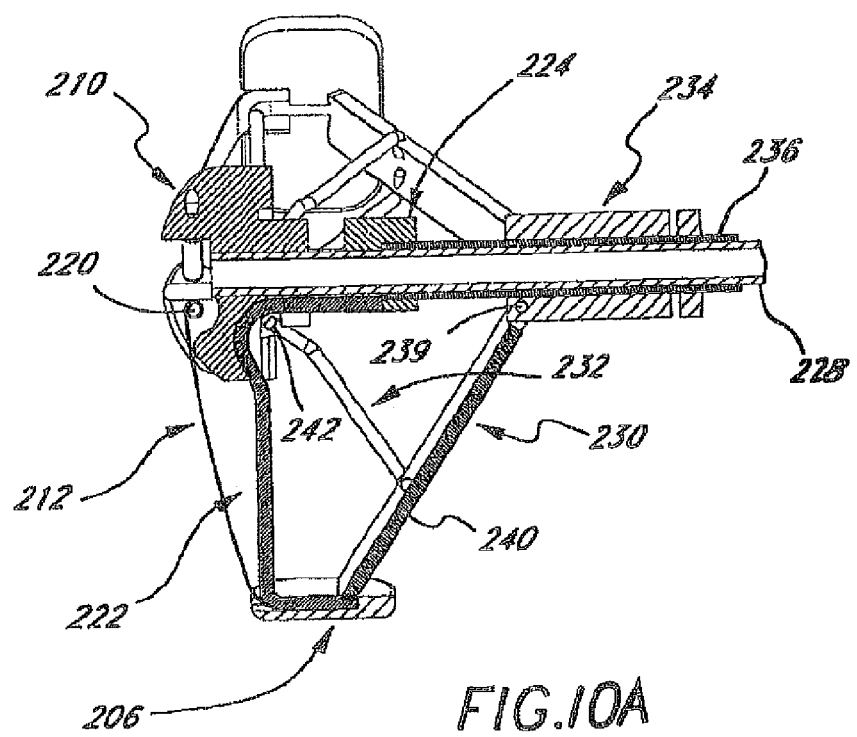
FIG. 10A is an enlarged sectional view of a portion of the distal end of the second alternative delivery and deployment system as taken along line 10A-10A of FIG. 10.

FIG. 10 illustrates the deployment mechanism 204 in a deployment stage that converts the heart valve from its initial expanded configuration to its final, locked out configuration. FIG. 10A is a longitudinal sectional view taken along line 10A-10A of FIG. 10 and shows in detail the various components of the distal end of the deployment mechanism 204. The distal end cap 210 is shown having a recess in its distal end that houses a plurality of shafts 220 about which coils each tension spring 212. The radial position of each pad 206 is controlled by use of a distal wire tong 222 that is highly flexible but possesses column strength. Various nickel-titanium alloys are well-suited for use as the wire tongs 222. Each tong 222 attaches to an inner side of a distal pad 206 and extends radially inward through a 90 degree channel formed in the distal end cap 210 into fixed engagement with a tong driver 224. The tong driver 224 attaches to a tong driver shaft 226 and is adapted for axial movement within the mechanism 204. The tong driver shaft 226 fits closely and is linearly slidable over a distal end cap shaft 228 fixed to a bore in the end cap 210. The distal end cap shaft 228 includes a lumen that closely receives a guidewire (not shown) used in positioning the heart valve at the site of implantation.

For the purpose of describing radial movement of the distal pads 206 with reference to FIG. 10A, the reader will ignore the interposition of a plurality of expansion bars 230 and brace links 232. Initially, the tong driver 224 is positioned to the right of where it is located in FIG. 10A and toward a distal slide collar 234. As such, the majority of the distal wire tong 222 is pulled through the distal end cap 210 such that its radial length is minimized, in contrast to the illustration. Therefore, the distal pads 206 are pulled radially inward and constrain the heart valve in its spirally wound configuration. During regulating self-expansion of the valve, the tong driver shaft 226 is advanced in the distal direction with respect to the end cap shaft 228 such that the tong driver 224 moves to the left, pushing the distal wire tongs 222 radially outward. Because of the column strength of the wire tongs 222, this operation forces the distal pads 206 radially outward against the inward forces of the tension springs 212, and permits the spirally wound valve to unwind.

The final outward position of the distal and proximal pads 206, 208 is seen in FIG. 9. FIG. 9 also illustrates the distal tong shaft 226 and the distal end cap shaft 228, along with a proximal tong shaft 236 and a proximal end cap shaft 238. Again, regulated self-expansion of the heart valve is accomplished by holding the end cap shafts 228, 238 stationery, while displacing the tong shaft 226, 236 away from one another. Because the pads 206, 208 displace directly radially outward, there is no need for any accommodating axial movement as with the earlier pivoting finger embodiments.

After permitting the heart valve 202 to self-expand to its initial expanded configuration as seen in FIG. 8, the pads 206, 208 are repositioned inside the valve and displaced outward to force the valve further outward into its final, expanded configuration. The position of the deployment mechanism 204 in this phase of the deployment operation is seen in FIGS. 10 and 10A. It will be noted that various components of the distal end of the deployment mechanism 204 will be numbered the same on the proximal end.

As seen in FIG. 10A, each of the expansion bars 230 pivots at one end about a point 239 on the respective slide collar 234. The opposite end of each expansion bar 230 is free to pivot radially outward into contact with the inner side of one of the pads 206, 208. Each brace link 232 pivots at one end about a point 240 at the midpoint of an expansion bar 230, and at the other and about a pivot point 242 fixed with respect to one of the end caps 210. Axial movement of the end caps 210 toward one another causes the expansion bars 230 to pivot outward by virtue of their connection to the end caps through the brace links 232. This umbrella-like expansion structure provides substantial strength in forcing the heart valve 202 into its locked out position.

FIGS. 11A-11F illustrate several stages in the use of the second alternative deployment mechanism 204 to deliver and deploy the heart valve 202. FIG. 11A shows the assembly in its radially contracted configuration for delivery through the patient's vasculature. FIG. 11B illustrates release of the wire tongs to push the pads radially outward which permits controlled self-expansion of a heart valve to its initial expanded configuration. In FIG. 11C, the end caps are axially displaced away from one another so that the pads disengage from the heart valve. In this regard, the tension provided by springs 212, 216 on the pads 206, 208 provides an axial force that helps disengage the pads from between the valve and the surrounding tissue. At this stage, the wire tongs remain pushed radially outward. FIG. 11D shows the end caps in the same axial position but after the wire tongs have been retracted such that the tension springs pull the pads inward. In FIG. 11E, the end caps are displaced axially toward one another which causes the expansion bars to pivot outward, and in addition, the pads moved inside the valve. Finally, FIG. 11F shows further end cap movement toward each other such that the expansion bars push the pads radially outward in conjunction with movement of the wire tongs so as to further expand the valve into its locked out configuration.

Figure 12:
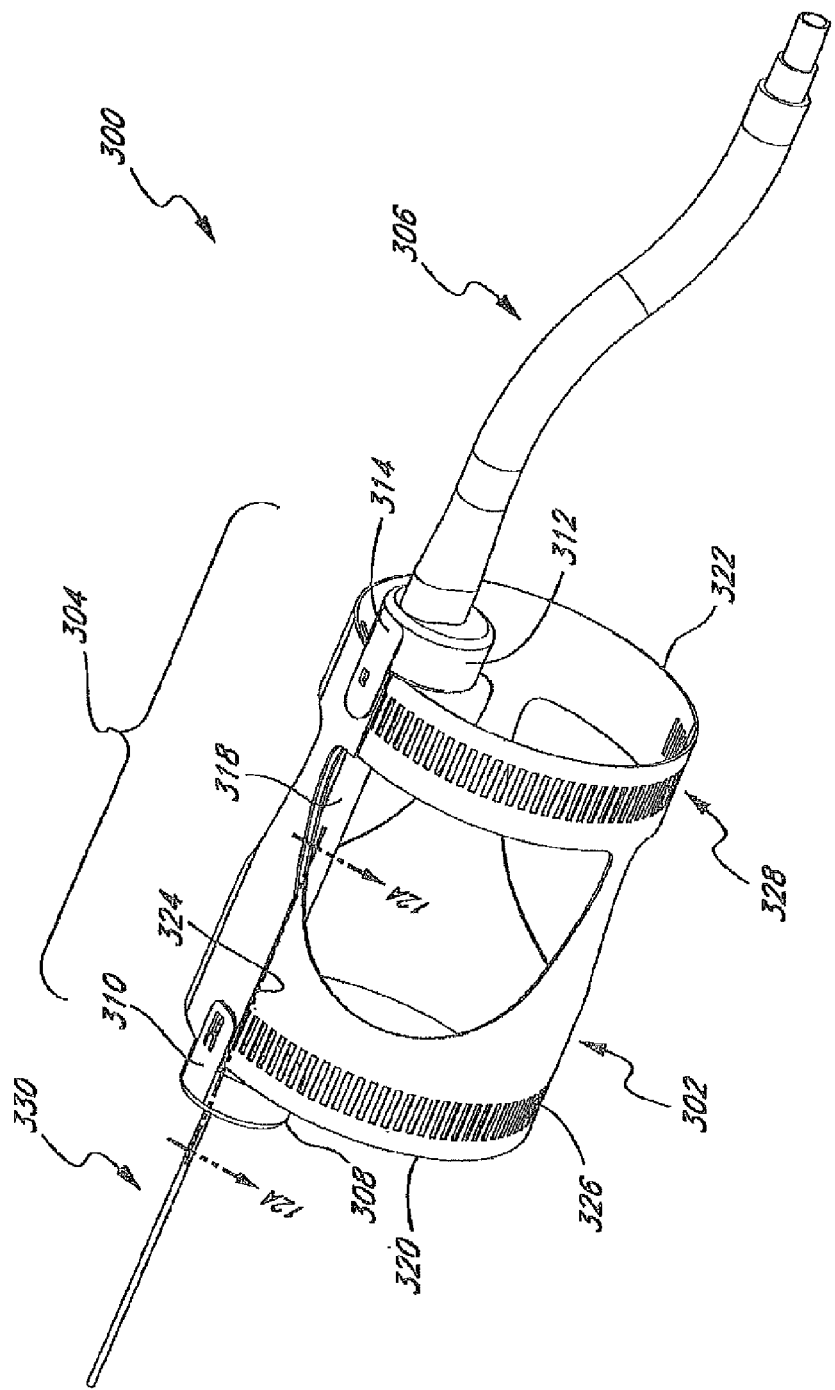
FIG. 12 is a perspective view of the distal end of a third alternative delivery and deployment system of the present invention that utilizes a gearing mechanism and showing a heart valve in its expanded configuration.

FIGS. 12-13 illustrate the distal end of a further alternative heart valve delivery and deployment system 300 that utilizes a gearing mechanism to expand a heart valve 302 into its initial and final expanded configurations. The system includes a deployment mechanism 304 at the distal end of a shaft 306 having a distal end keeper 308 and retaining bar 310 and a proximal end keeper 312 and retaining bar 314. The axial spacing between the distal and proximal end keepers 308, 312 may be varied by movement of a connecting rod 316 (FIG. 12A) about which a gear shaft 318 rotates. The heart valve 302 includes a sheet-like stent body bordered by a distal end 320, a proximal end 322, an outer side edge 324, and an inner side edge (not shown). The stent body further includes a distal gear track 326 extending circumferentially adjacent the distal end 320 and a proximal gear track 328 extending circumferentially adjacent the proximal end 322. The assembly rides over a guide wire 330 as mentioned previously.

Figure 12A:
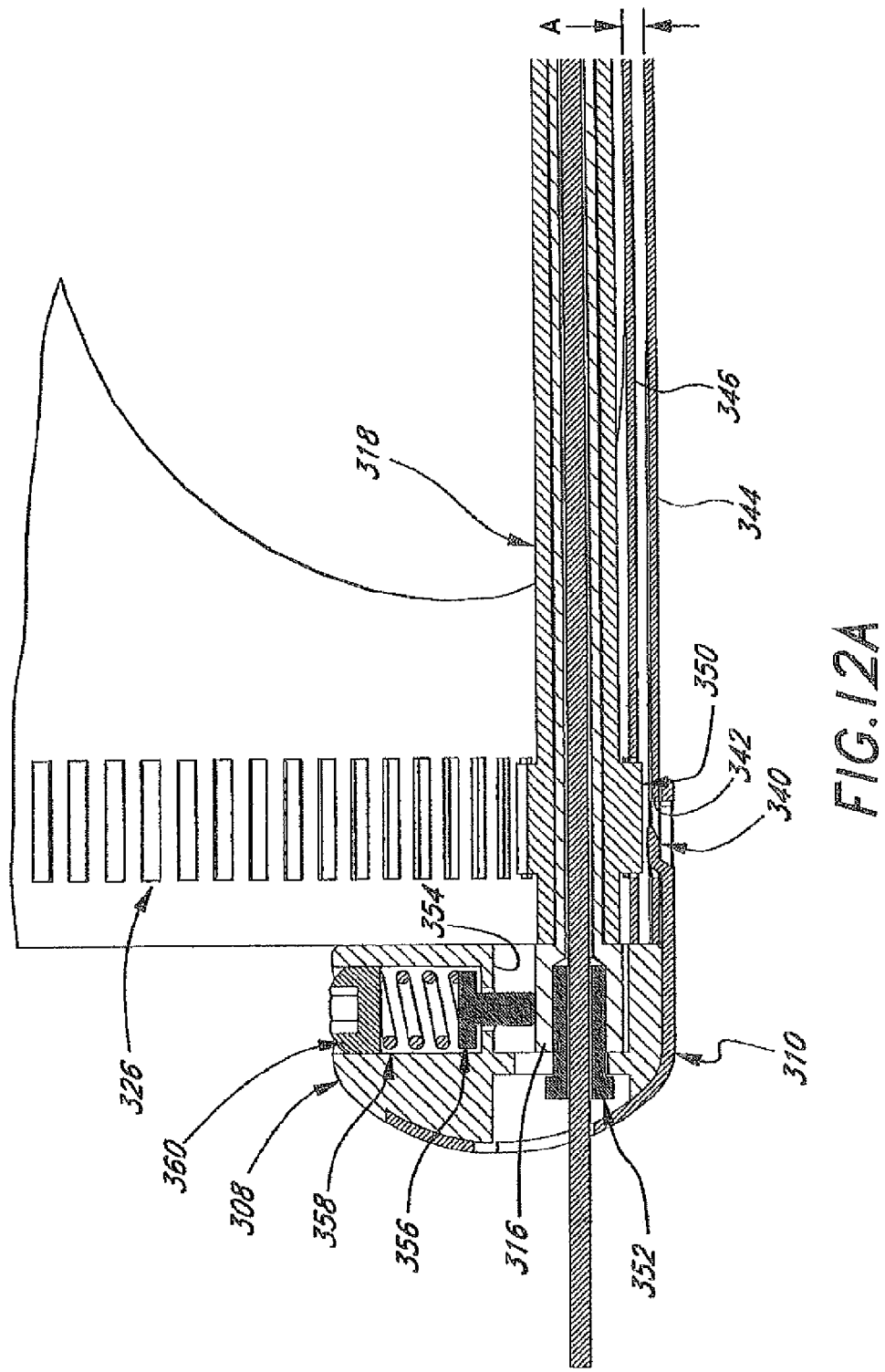
FIG. 12A is an enlarged sectional view of a portion of the distal end of the third alternative delivery and deployment system as taken along line 12A-12A of FIG. 12.

With reference to FIGS. 12A and 13, details of the distal end keeper 308 and retaining bar 310 will be described. The retaining bar 310 extends axially in a proximal direction from the end keeper 308 includes an inwardly formed tab 340 that engages a retaining slot 342 in an outer valve body winding 344 adjacent to the outer side edge 324. FIG. 12A illustrates in cross-section an inner winding 346 spaced from the outer winding 344 by a distance A. Of course, there may be more than two windings of the valve body in the contracted configuration thereof, as previously illustrated, for example, in FIG. 3A. Therefore, the distance A varies as the valve unwinds.

The gear shaft 318 includes gear teeth 350 positioned to engage the distal gear track 324. In a similar manner, a second set of gear teeth (not shown) is provided on the proximal end of the gear shaft 318 to engage the proximal gear track 326. As mentioned, the gear shaft 318 rotates about the connecting rod 316, which is held by a shaft retainer 352 in a winding variance slot 354 in the distal end keeper 308. The end of the connecting rod 316 includes a flat or other such feature that registers with a cooperating feature in the winding variance slot 354 to prevent rotation of the rod, and provide a counter-torque to rotation of the gear shaft 318. The slot 354 is elongated in the radial direction to permit radial movement of the connecting rod 316 and accompanying gear shaft 318. Provision of a pusher 356 spring loaded against the connecting rod 316 by a spring 358 and set screw 360 maintains the gear teeth 350 in engagement with the gear track 324.

With reference to FIG. 12, it can be seen that the deployment mechanism 304 remains circumferentially fixed with respect to the outer side edge 324 by virtue of the engagement between the retaining bar tabs 340 and retaining slots 342. The gear shaft 318, on the other hand, circumferentially displaces the inner winding 346 in a direction that unwinds the valve from its contracted configuration to its expanded configuration. During the unwinding process, the distance A between the outer winding 34 and the inner winding 346 is regulated by the spring loaded pusher 356. The valve 302 may be converted to its initial expanded configuration, and then further balloon expanded to a final lockout position, or the deployment mechanism 304 can fully expand the valve into its lockout position. When the deployment mechanism 304 is no longer needed, the end keepers 308, 312 are displaced axially apart such that the retaining bars 310, 314 disengage from their respective retaining slots 342. The deployment mechanism 304 can then be pulled over the guide wire 330 from within the deploying valve.

One advantage of such a deployment system 300 that utilizes a gearing mechanism is that both unwinding and winding of the valve 302 may be easily controlled. Therefore, the surgeon may initially expand the valve 302 but then contract it somewhat to modify its position prior to locking it into its final expanded shape. In the worst case, the valve 302 may be completely contracted into its thin profile and removed from the patient if desired, such as if the sizing is not optimal or from other complications.

FIG. 14 illustrates in plan view an exemplary aortic valve body 400 for use with a deployment mechanism similar to that shown in FIG. 12. The valve body 400 includes a distal end 402, a proximal end 404, an inner side edge 406, and an outer side edge 408. A distal gear track 410 is shown adjacent the distal end 402, while a proximal gear track 412 extends along an outflow band 414. A plurality of leaflet openings 416 is provided between the distal end 402 in the outflow band 414. A flared mesh 418 separates the outflow band 414 from the proximal end 404. A supplemental gear track 420 is provided adjacent the proximal end 404. The distal, proximal, and supplemental retaining slots 422, 424, 426 are located adjacent the outer side edge 408 and receive respective retaining tabs from the retaining bars of the deployment mechanism. Finally, lockout tabs 430 are provided to engage lockout channels 432 and maintain the valve in its expanded configuration.

In contrast to the valve 302 shown FIG. 12, the flared mesh 418 extends in the outflow direction and may be used to engage the ascending aorta. To facilitate flaring of the mesh 418 during deployment of the valve, the supplemental gear track 420 has a smaller number of openings per length than the distal or proximal gear tracks 410, 412. Likewise, the gear shaft utilized in deploying the valve body 400 has three sets of gear teeth, one of which has fewer teeth per rotation so as to mate with the supplemental gear track 420. In this manner, the proximal end 404 is expanded at a faster rate then either the distal end 402 or outflow band 414 such that it flares outward with respect thereto.

While the foregoing describes the preferred embodiments of the invention, various alternatives, modifications, and equivalents may be used. Moreover, it will be obvious that certain other modifications may be practiced within the scope of the appended claims.

What is claimed is:

1. A method for deploying a prosthetic valve in a patient's native aortic valve, the method comprising:

percutaneously advancing through a patient's vasculature a distal end portion of an elongate delivery system, a prosthetic valve in a contracted configuration disposed on the distal end portion, the prosthetic valve comprising a radially contractible and expandable tubular stent made from a nickel-titanium alloy and a plurality of leaflets secured to the stent, the plurality of leaflets made from bovine pericardium, the stent coupled to a deployment mechanism disposed on the distal end portion, the deployment mechanism comprising a longitudinally extending shaft and proximal and distal retaining components coupled to proximal and distal end portions of the stent, the shaft rotatable with respect the proximal and distal retaining components;

positioning the prosthetic valve in an annulus of a native aortic valve;

rotating the shaft of the deployment mechanism in a first direction, thereby expanding the prosthetic valve to a final expanded configuration within the annulus of the native aortic valve; and actuating lockout features on the prosthetic valve to lock the prosthetic valve in the final expanded configuration.

2. The method of claim 1, further comprising:

before rotating the shaft of the deployment mechanism in the first direction, rotating the shaft in the first direction to expand the prosthetic valve from the contracted configuration to an initial expanded configuration;

rotating the shaft in a second direction opposite the first direction, thereby re-contracting the prosthetic valve from the initial expanded configuration; and repositioning the prosthetic valve.

3. The method of claim 1, further comprising disengaging the delivery system from the prosthetic valve and removing the delivery system from the patient.

4. The method of claim 3, wherein disengaging the delivery system further comprises disengaging at least a portion of the deployment mechanism.

5. The method of claim 1, wherein percutaneously advancing the prosthetic valve comprises percutaneously advancing the prosthetic valve over a guide wire.

6. The method of claim 1, wherein the prosthetic valve is self-expandable.

7. A method for deploying a prosthetic valve in a patient's native aortic valve, the method comprising:

percutaneously advancing through a patient's vasculature a distal end portion of an elongate delivery system, a prosthetic valve in a contracted configuration disposed on the distal end portion, the prosthetic valve comprising a radially contractible and expandable tubular stent and a plurality of leaflets secured to the stent, the stent coupled to a deployment mechanism disposed on the distal end portion, the deployment mechanism comprising a longitudinally extending shaft, the shaft rotatable about a longitudinal axis thereof;

positioning the prosthetic valve in an annulus of a native aortic valve; and rotating the shaft of the deployment mechanism in a first direction, thereby expanding the prosthetic valve to a final expanded configuration within the annulus of the native aortic valve, wherein the shaft further comprises a set of gear teeth and the stent comprises a gear track positioned to engage the gear teeth.

8. A method for deploying a prosthetic valve in a patient's native aortic valve, the method comprising:

percutaneously advancing through a patient's vasculature a distal end of an elongate delivery system, a prosthetic valve in a contracted configuration disposed on the distal end portion, the prosthetic valve comprising a radically contractible and expandable tubular stent and a plurality of leaflets secured to the stent, the stent coupled to a deployment mechanism disposed on the distal end portion, the deployment mechanism comprising a longitudinally extending shaft, the shaft rotatable about a longitudinal axis thereof;

positioning the prosthetic valve in an annulus of a native aortic valve; and rotating the shaft of the deployment mechanism in a first direction, thereby expanding the prosthetic valve to a final expanded configuration within the annulus of the native aortic valve, wherein the shaft comprises a distal set of gear teeth and a proximal set of gear teeth, and the stent comprises a distal gear track and a proximal gear track, the distal set of gear teeth positioned to engage the distal gear track and the proximal set of gear teeth positioned to engage the proximal gear track.

9. A method for deploying a prosthetic valve in a patient's native aortic valve, the method comprising:

advancing a prosthetic valve through a patient's vasculature, the prosthetic valve comprising a radially contractible and expandable tubular stent body made from a nickel-titanium alloy and a plurality of leaflets made from bovine pericardium, the prosthetic valve coupled to a deployment mechanism positioned along a distal end portion of an elongate delivery system, the deployment mechanism comprising a plurality of retaining mechanisms and a rotatable shaft, the shaft being rotatable with respect to the retaining mechanisms;

positioning the prosthetic valve adjacent an annulus of a native aortic valve;

rotating the shaft relative to the retaining mechanisms for causing the prosthetic valve to expand in the annulus of the native aortic valve; and locking the prosthetic valve in a final expanded configuration;

wherein the retaining mechanisms remain circumferentially fixed with respect to at least a portion of the stent body while the shaft is rotated to provide regulated expansion of the prosthetic valve in the annulus of the native aortic valve.

10. The method of claim 9, wherein the retaining mechanisms are axially displaced for disengaging the retaining mechanisms from the stent body.

11. The method of claim 10, wherein the retaining mechanisms comprise tabs and the stent body comprises slots.

12. The method of claim 9, wherein the elongate delivery system is advanced over a guidewire for advancing the prosthetic valve through the patient's vasculature.

13. The method of claim 9, wherein the shaft is rotated using a proximal operating handle.

14. The method of claim 9, wherein the prosthetic valve partially self-expands before rotating the shaft.

15. The method of claim 9, wherein the prosthetic valve is advanced through the patient's vasculature while visualizing at least one radiopaque marker located on the stent body.

16. The method of claim 9, wherein the shaft is capable of being rotated in an opposite direction for contracting the prosthetic valve and modifying the position of the prosthetic valve before locking the prosthetic valve in the final expanded configuration.

* * * * *

UNITED STATES PATENT AND TRADEMARK OFFICE
CERTIFICATE OF CORRECTION

PATENT NO. : 9,572,663 B2
APPLICATION NO. : 14/203258
DATED : February 21, 2017
INVENTOR(S) : Jibin Yang et al.

Page 1 of 1

It is certified that error appears in the above-identified patent and that said Letters Patent is hereby corrected as shown below:

In the Claims

In Claim 8, Line 7, correct "radically" to read --radially--.

Signed and Sealed this
Nineteenth Day of September, 2017

Joseph Matal
*Performing the Functions and Duties of the
Under Secretary of Commerce for Intellectual Property and
Director of the United States Patent and Trademark Office*